United States Patent [19]

Lazarus et al.

[11] Patent Number: 5,780,589
[45] Date of Patent: Jul. 14, 1998

[54] ULTRASELECTIVE OPIOIDMIMETIC PEPTIDES AND PHARMACOLOGICAL AND THERAPEUTIC USES THEREOF

[75] Inventors: Lawrence H. Lazarus, Durham, N.C.; Severo Salvadori, Ferrara; Piero Andrea Temussi, Naples, both of Italy

[73] Assignee: The United States of America as represented by the Department of Health and Human Services, Washington, D.C.

[21] Appl. No.: 347,531

[22] Filed: Nov. 30, 1994

[51] Int. Cl.$^6$ ..................................... A61K 38/06
[52] U.S. Cl. ........................ 530/331; 514/18; 514/19
[58] Field of Search ..................... 514/18, 19; 530/331

[56] References Cited

U.S. PATENT DOCUMENTS 5,455,230  10/1995  Schiller .................... 514/18

FOREIGN PATENT DOCUMENTS 0 136 720  4/1984  European Pat. Off.
0 215 297  12/1986  European Pat. Off.
WO 94/15959  7/1994  WIPO.

OTHER PUBLICATIONS

Barnett S. Pitzele, et al., (1994) "Enkephalin Analogs as Systemically Active Antinociceptive Agents: O–and N–Alkylated Derivatives of the Dipeptide Amide L-2, 6-Dimethyltryosyl-N-(3-phenylpropyl)-D-alaninamdie" *J. Med. Chem.* 37, 888–896.

P. Amodeo et al., (1995) "Confirmation analysis of potent and very selective δopiod dipeptide antagonists" *FEBS Letters* 377:363-367.

S. Salvadori et al.(1995) "δOpioidmimetic Antagonists: Prototypes for Designing a New Generation of Ultraselective Opoid Peptides" *Molecular Medicine* 1076-1551/95 678–689.

M.R. Ciajolo, et al. "Solution and solid–state structure of the diketopiperazine of tyrosyl–tetrahydroisoquinoline–3–caboxylic acid" *International Journal of Peptide & Protein Research* 1995, 46, 134–138.

Lazarus, L.H., et al., (1994) "Frog Skin Opioid Peptides: A Case for Environmental Mimicry" *Environmental Health Perspectives*, vol. 102, pp. 648–654.

Lazarus, L.H. And Attila, M., (1993) "The Toad, Ugly and Venomous, Wears Yet A Precious Jewel in His Skin" *Progress in Neurobiology* , vol. 41, pp. 473–507.

Temussi, P.A., et al., (1994) "Selective Opiod Dipeptides" *Biochem. and Biophys. Res. Comm.*, vol. 198, pp. 933–939.

Lazarus, L.H., et al., (1992) "Stereospecificity of Amino Acid Side Chains in Deltorphin Defines Bindings to Opioid Receptors" *J. Med. Chem.*, vol. 35 pp. 1222–1227.

Lazarus, L.H., et al., (1989) "Dermorphin Gene Sequence Peptide with High Affinity and Selectivity for δ–Opioid Receptors" *J. Biol. Chem.*, vol. 264 pp. 3047–3050.

Salvadori, S., et al., (1993) "Phe$^3$ –Substituted Analogues of Deltorphin C. Spatial Conformation and Topography of the Aromatic Ring in Peptide Recognition by δOpioid Receptors" *J. Med. Chem.*, 36 pp. 3748–3756.

Hammond, D.L. et al., "Antinociception Produced By Oral, Subcutaneous Or Intrathecal Administration of SC–39566, An Opioid Dipeptide Arylalkylamide, In The Rodent$^1$ ", *J. Pharmacol. Exper. Ther* 268:607–615.

Schiller, P.W. et al., (1991) Conformationally Restricted Deltorphin Analogues†, ‡ *J. Med. Chem.* 35:3965–3961.

Portoghese, P.S. (1989) "Bivalent Ligands And The Message—Address Concept In The Design Of Selective Opioid Receptor Antagonists" *Trend's Phar. Sci.* 10:230–235.

Deeks, T. et al., (1983) "Synthesis and Analgesic Properties of Two Leucine–Enkephalin Analogues Containing a Conformationally Restrained N–Terminal Tyrosine Residue" *J. Med. Chem.* 26:762–765.

Hruby V.J. et al. (1989) "Recent Developments in the Design of Receptor Specific Opioid Peptides." *Med. Res. Rev.* 9,343–401.

Schiller, P.W., et al. (1993) TIPP[ψ]: A Highly Potent and Stable Pseudopeptide δ Opioid Receptor Antagonist With Extraordinary δSelectivity. *J. Med. Chem.* 36, 3182–3187.

Chandrakumar N.S., et al. (1992) "Preparation And Opioid Activity Of Analogues Of The Analgesic Dipeptide 2,6-Dimethyl–L–tyrosyl–N–(3–phenylpropyl)–D–alaninamide." *J. Med. Chem.* 35, 223-233.

Chandrakumar N.S., et al. (1992) "Analogs Of The δ Opioid Receptor Selective Cyclic Peptide [2–D–penicillamine, 5–D–penicillamine]enkephalin:2',6'–dimethyltrosine and Gly$^3$ –Phe$^4$ Amide Bond Isostere Substitutions." *J. Med. Chem.* 35, 2928–2938.

Mosberg H.I., et al. (1992) Incorporation Of A Novel Conformationally Restricted Tyrosine Analog Into a Cyclic, δ Opioid Receptor Selective Tetrapeptide (JOM–13) Enhances δ Receptor Binding Affinity And Selectivity. *J. Med. Chem.* 35, 4498–4500.

Lazarus L.H., et al. (1991) "Opioid Receptor Selectivity Reversal In Deltorphin Tetrapeptide Analogues." *Biochem. Biophys. Res. Commun.* 178, 110–115.

Marastoni M., et al. (1991) "On the Degradation Of Deltorphin Peptides By Plasma And Brain Homogenates." *Farmaco* 46, 1273-1279.

Temussi P.A., et al. (1994) "Selective Opioidi Peptides." *Biochem. Biophys. Res. Commun.* 198, 933–939.

Schiller, Proc. 13th Amer Pept Symp (1994) pp. 483–486.

Primary Examiner—David Lukton
Attorney, Agent, or Firm—Morgan & Finnegan

[57] ABSTRACT

Novel opioidmimetic dipeptides, tripeptides and cyclic peptides exhibit enhanced affinity and selectivity for δ opioid receptors. The peptides are represented by the formulas L/D-Dmt-L-/D-Tic-R', L/D-Dmt-L-/D-Tic-R-R' and cyclic (L/D-Dmt-L/D-Tic) wherein Dmt is 2',6'.-dimethyl-L/D-tyrosine Tic is L-/D-1,2,3,4-tetrahydroisoquinoline-3-carboxylic acid, R is a natural or unusual aliphatic amino residue and R' is a functional group at the carboxyl terminus of the peptide. Pharmacological and therapeutic and compositions are also provided.

23 Claims, 3 Drawing Sheets

ULTRASELECTIVE OPIOIDMIMETIC PEPTIDES AND PHARMACOLOGICAL AND THERAPEUTIC USES THEREOF

FIELD OF THE INVENTION

This invention relates to opioidmimetic peptides that are characterized by a high degree of selectivity for opioid receptors. More specifically this invention relates to novel dipeptides, tripeptides and cyclic peptides containing 2',6'-dimethyl-L-tyrosine and 1,2,3,4-tetrahydro-3-isoquinoline carboxylic acid at positions 1 and 2 respectively, having ultraselective delta (δ) receptor activity and to pharmacological, and therapeutic uses thereof.

BACKGROUND OF THE INVENTION

The existence of three major opioid receptor types (δ, µ and κ) was recognized in pharmacology through structure-activity applications using large numbers of enkephalin and dynorphin analogues (1,2), and the amphibian skin-derived opioids (3). The distinct structural differences between these 7 transmembrane spanning receptor proteins were recently verified by cDNA cloning and sequencing (4–15); one of the cloned δ receptors corresponds to the pharmacologically identified $δ_2$ receptor subtype (10,16–18). Selective agonists and antagonists for specific receptor types nonetheless continue to provide key tools for understanding the therapeutic and medicinal applications in combating addictive narcotics in human health and unraveling the role of opioid receptors in opiate addiction and tolerance (19), as well as in pharmacological, physiological and biochemical processes. Despite the advancements made through the improvement of the selectivity of enkephalins by incorporation of D-enantiomeric amino acids and conformationally constrained cyclic peptides (1,2), the amphibian heptapeptides with the common N-terminal tripeptide sequence (Tyr-D-Xaa-Phe) (SEQ ID NO:1) represented the most potent µ or δ selective opioid peptides known (3); whereas dermorphins are µ selective, the deltorphins are highly δ selective (3). The reversed selectivity (δ→µ) in deltorphins resulting from truncation of the C-terminal region, provided evidence that the tetra- (20,21–26) and tripeptides (25) contained the essential information for µ selectivity (22,27–29). Thus, it became evident that only the N-terminal portion of the peptide was required to elicit an opioid response in linear or cyclic tetrapeptide analogues (30,31).

The amino acid sequence of the amphibian opioid peptides provided evidence for the requirement of an aromatic benzyl side-chain at position 3 (31,32) rather than position 4 which occurs in enkephalin (1,2). Replacement with D-enantiomers (33), and modifications of the hydrophobic content of the C-terminal region of the deltorphins (22,27, 34–36) provided further evidence on the acquisition of high δ affinities and selectivities. However, substitution of aromatic bicyclic constrained residues of position 3 enhanced or maintained δ affinities and selectivities (30,31). These studies were instrumental in the eventual development of tri- and tetrapeptides containing tetrahydro-3-isoquinoline carboxylic acid (Tic) at position 2 in the Tyr-L-/D-Tic-Phe-(Phe)—OH (SEQ ID NO:2) pseudopeptides, which exhibited selectivity for either the µ or δ receptor depending on the chirality of Tic (37,38).

Recently, Tyr-Tic-NH$_2$ (SEQ ID NO:3) and Tyr-Tic-Ala-NH$_2$/—OH (SEQ ID NO:4) (by convention if the stereochemistry is not specified, the residue is taken to be L) were designed as δ antagonists via conformational analysis in a search for low energy conformers in comparison with rigid models for consistency with biological requirements (39). They exhibit opioid activity and lack an aromatic residue at position 3 (39). The two groups of abbreviated Tic$^2$ (the superscript denotes the position of the residue in the peptide) analogues exhibited δ receptor antagonist properties in pharmacological preparations (39, 93).

Opioids and opioid receptors mediate a variety of effects in mammalian physiology including the production of analgesia, modification of the secretion of circulating peptide hormones, alteration of body temperature, depression of respiration, gastrointestinal function, and immune system activities. Opioids also have a wide range of therapeutic utilities, such as treatment of opiate and alcohol abuse, neurological diseases, neuropeptide or neurotransmitter imbalances, neurological and immune system dysfunctions, graft rejections, pain control, shock and brain injuries. Due to the comprehensive therapeutic applications of opioids for modulation of mammalian physiology, there is an enormous medical and health requirement for more potent, stable, and highly selective peptides that specifically bind opioid receptors.

SUMMARY OF THE INVENTION

This invention relates to novel opioidmimetic dipeptides, tripeptides and cyclic peptides. More specifically, the novel peptides of this invention exhibit ultraselective specificity and potency for the δ receptor. This invention also relates to therapeutic, pharmacological and physiological compositions of the peptides.

It is an object of this invention to provide novel dipeptides of the formula L/D-Dmt-L-/D-Tic-R'(SEQ ID NO:5), wherein R' is a functional group at the carboxyl terminus of the peptide.

It is another object of this invention to provide novel tripeptides of the formula L/D-Dmt-L/D-Tic-R-R'(SEQ ID NO:6) wherein R is a natural or unusual aliphatic, aromatic or ionic amino acid residue and R' is a functional group at the carboxyl terminus of the peptide.

It is yet another object of this invention to provide novel cyclic peptides of the formula c(L/D-Dmt-L/D-Tic) (SEQ ID NO:7) and c(L/D-Dmt-L/D-Tic-R) (SEQ ID NO:8) wherein R is a natural or unusual amino acid.

It is a further object of this invention to provide pharmaceutical compositions comprising the novel opioidmimetic dipeptides, tripeptides or cyclic peptides.

It is yet another object of this invention to provide pharmacological and therapeutic uses for these novel opioidmimetic, dipeptides, tripeptides or cyclic peptides and pharmacological compositions comprising the same.

DESCRIPTION OF THE FIGURES

FIG. 1 shows superimposition of the low energy conformers that represent each cluster family of Tyr-Tic-OH (peptide 12) Dmt-Tic-OH (peptide 1), and c(Dmt-Tic) (peptide 6) from top to bottom.

DETAILED DESCRIPTION OF THE INVENTION

The present invention provides novel opioidmimetic dipeptides, tripeptides and cyclic peptides that exhibit high selectivity, affinity and potency for the delta opioid receptor. By opioidmimetic peptides we mean peptides capable of binding to an opioid receptor. These novel peptides include those which function as either agonists, partial agonists, antagonists, partial antagonists or have mixed antagonist/agonist-activity for opioid receptors.

The dipeptides have the formula: L/D-Dmt-L/D-Tic-R' (SEQ ID NO:5); wherein

R' is a functional group at the carboxyl terminus of the peptide.

Examples of functional groups include, but are not limited to, amides (NH$_2$,), isoamylamide, carboxylic acids (—COOH), methoxy (—OMe), ethoxy (—OEt), 1-adamantane, 1-adamantanecarbonyl hydrazide, alcohols (—CH$_2$OH) acetyl hydrazide, (—NH—NH—CO—CH$_3$ ), methyl (—CH$_3$), cyano, (—CN), azide (—N$_3$), and esters, alkenes, alkynes, alkyls, and various protective groups. Most preferred functional groups are —NH$_2$, —OH and —CH$_2$OH. Examples of protecting groups include, but are not limited to, tert-butyloxycarbonyl (Boc), tert-butyl (tBu), N-9-fluoroenylmethylozycarbonyl (Fmoc), benzylcarbonyl (Z), benzyl ester (OBzl), tert-butyl ester (OtBu), benzyl (Bz), methyl ester (OMe) and amide (NH$_2$). Preferred peptides of this formula are L/D-Dmt-L/D-Tic-OH and L/D-Dmt-L/D-Tic-NH$_2$. A preferred configuration is L at the second position.

The tripeptides have the formula:

L/D-Dmt-L/D-Tic-R-R'(SEQ ID NO:6)

wherein

R is a natural or unusual amino acid and R' is a functional group at the carboxyl terminal residue of the peptide. Examples of a natural amino acid include, but are not limited to, any one of the twenty naturally occurring amino acids and their enantiomers. By way of example, amino acids such as histidine, or glycine; aliphatic amino acids, such as leucine, isoleucine, valine; acidic amino acids, such as glutamic acid, aspartic acid; sulfur containing amino acids, such as cysteine, methionine; hydroxyl amino acids, such as serine, threonine, aromatic and ring structured amino acids, such as tryptophan, phenylalanine, and tyrosine; amide residues, such as asparagine, glutamine; basic residues, such as lysine, arginine; and cyclic imino, such as proline, may be used for R.

By unusual amino acid we mean any amino acid which is not one of the twenty naturally occurring amino acids. Examples of unusual amino acids include, but are not limited to, aminoisobutyric acid, aminobutyric acid, diaminobutyric acid, γ-carboxyglutamic acid, Tic, 2-aminoindane-2-carboxylic acid (Aic), 2-aminotetraline-2-carboxylic acid (Atc), homophenylalanine (Hfe), 1- and 2-naphthylalanines (Nap), dehydrophenylalanine (ΔPhe), methylphenylalanines, methylhistines, and halogenated and boronyl amino acids.

Examples of functional groups include but are not limited to, amides (—NH$_2$,), isoamylamide, carboxylic acids (—COOH), methoxy (—OMe), ethoxy (—OEt), 1-adamantane, 1-adamantanecarbonyl hydrazide, alcohols (—CH$_2$OH) acetyl hydrazide, (—NH—NH—CO—CH$_3$ ), methyl (—CH$_3$), cyano, (—CN), azide (—N$_3$), and esters, alkenes, alkynes, alkyls, and various protective groups.

Examples of protective groups include but is not limited to Boc, tBu, Fmoc, Z, OBzl, OtBu, Bz, OMe and NH$_2$. Preferred peptides of this formula are L-Dmt-L/D-Tic-Ala-NH$_2$ (SEQ ID NO:9) or L-Dmt-L/D-Tic-Ala-OH (SEQ ID NO:10). A preferred configuration for the tripeptides is L in the second position.

The cyclic peptides have the formula:

c(L-/D-Xmt-L-/D-Yaa) (SEQ ID NO:11); or c(L-/D-Xmt-L-/D-Yaa-R) (SEQ ID NO:12)

wherein R and Yaa can be any natural occurring amino acid or unusual amino acid, and Xmt can be monomethyl (Mmt), dimethyl (Dmt), or trimethyl (Tmt). Examples of an amino acid include, but are not limited to, any of the naturally occurring amino acids and their enantiomers. Tic, Phe, 2-aminoindane-2-carboxylic acid (AIC), or 2-amino-2-tetralane-2-carboxylic acid. A preferred peptide of this formula is c(L-Dmt-L-Tic).

Also intended to be encompassed by this invention are analogues of the novel peptides. By analogues we mean substitution of one residue for another which maintains or enhances the affinity and/or specificity of the peptide. By way of example, a change in chirality at residue 2 (L- to D-Tic) and that of R at position 3 from the L- to D-enantiomer, either as simultaneous or independent changes is considered an analogue. In addition to changes in chirality of Dmt (L→D) or use of NMe-Dmt, other modifications of residue 1 are also intended to be encompassed by this definition. By analogues we also mean a change in chirality of one of the residues, or a terminal substitution. Also intended to be encompassed by analogues are peptides which have been modified to include protecting groups, such as examples of protective groups include but is not limited to DIC, PyBrOP, Buc, tBu, Fmoc, Z, OBzl, OtBu, Bz, OMe and NH$_2$ radioactive labeled molecules, such as $^3$H (tritium) and $^{14}$C (Carbon 14), colorimetric molecules, such as fluorescamine and other conventional dyes.

The peptides of this invention exhibit many advantages over other reported peptides that bind to opioid receptors. Dmt-Tic-OH (peptide 1; Table III)) and Dmt-Tic-Ala-OH (peptide 8; Table III) demonstrate higher potency, enhanced selectivity, and higher affinity for the δ receptor than other known peptides. In addition, in comparison to the Tyr-Tic cognates, the novel linear Dmt peptides induced an 8,500-fold increase in δ affinity and 1,000-fold in selectivity relative to Tyr-Tic-OH (peptide 12; Table II); δ selectivity of Dmt-Tic-OH (peptide 1; Table II) was approximately two orders of magnitude greater than that reported for the deltorphins (20,22,27,32–34,40–43). In concert with these observations on the Tyr-Tic peptides (39) and TIPP analogues (37,38), the amidated Dmt-Tic (Dmt-Tic-NH$_2$; peptide 2, Table III) and Dmt-D-Tic di-and tri peptides (Table III and Table IV) increased μ affinity, thereby resulting in a loss or reversal of selectivity (δ→μ); D-Tic also causes an increase in μ affinity. Analysis of the cyclic peptides revealed that the δ affinity of c(Dmt-Tic) was 4,000-fold higher than c(Tyr-Tic); peptide 17), δ selectivity was less than that of the non-cyclic linear Dmt-Tic peptides. These Dmt-Tic structures therefore represent a new and potent class of δ selective peptides which have a minimal structure and optimally fit the internal environment of the δ receptor pocket with high affinity and fidelity.

Susceptibility to enzymatic proteolysis results in short half-lives for most peptides. Another advantage related to the novel peptides of this invention, is prolonged half life of their peptides. Without being bound by theory, the increased stability is due to the presence of D-isomers or L-isomers of unusual amino acids which enhance the half-life of a peptide, some of which are completely resistant to degradation in mammalian tissues or sera.

Whether the novel opioidmimetic peptides of the present invention function as agonists, partial agonists, antagonist or partial antagonists can be determined by conventional techniques known to those skilled in the art. Examples of such in vitro techniques include, but not as limited to, mouse vas deferens assay for δ assays and guinea-pig ileum for μ assays (32,50). Examples of in vivo studies, include, but is not limited to, the tail flick test (52,54) which can be used to determine if a peptide is an agonist or an antagonist by its ability to block or reverse opiates, such as morphine, naltrindole and its derivatives. By way of example, the peptides may be administered by subcutaneous or intravenous or by intraceberal ventricular administration routes. Peptides 1, 2, 5, 6, 8 and 9 (see Table VI) elicited antagonist properties in the in vitro mouse vas deferens bioassay. Dmt-Tic-Ala-OH (peptide 8) produced analgesia upon subcutaneous (sc) administration. Dmt-Tic-OH (peptide 1) produced no demonstratable analgesia by the tail flick test, it completely blocked the effect of morphine injected intravenously in keeping with the antagonist effect observed in vitro (Table VI).

The peptides of this invention can be synthesized by standard methods known to one skilled in the art ("Modern Techniques of Peptide and Amino Acid Analysis, John Wiley & Sons (1981); M. Bodansky" Principles of Peptide Synthesis" Springer Verlag (1984)). In one embodiment the peptides of the present invention can be synthesized by the Merrifield solid phase methodology and known variations thereof. In an alternative embodiment the peptides of the invention may be synthesized by the solution method (32) or variations thereof. The peptide coupling agents and protecting groups used in the synthesis of the peptides are well known to one of skill in the art. Examples of coupling agents include, but are not limited to, 1-ethyl-3-(3-dimethylaminopropylcarbodiimide (DCC) and diisopropyl carbodiimide (DIPI). Examples of protecting groups include, but are not limited to, PyBrOP, BOC, tBu, Fmoc, Z, OBzl, OtBu, Bz, OMe, and $NH_2$ (T. Greene "Protective Groups in Organic Synthesis" Academic Press (1981)). One of skill in the art will appreciate that the cyclic analogues cannot react with an acid group since there are no basic groups present.

Once the desired peptide is synthesized the peptide may be isolated from the reaction mixture and purified by a variety of standard methods. Examples of isolation and purification methods include, but are not limited to, crystallization, high pressure liquid chromatography, affinity chromatography, and open column silica chromatography.

Studies characterizing drugs or peptides as agonist or antagonist or partial agonists a partial antagonist require the use of other peptides as competing ligands. The peptides of the current invention exhibit a high degree of selectively and affinity for the $\delta$ receptor. Thus, the peptides of the present invention may be used as competitors in assays involving the $\delta$ receptor. Alternatively the opioidmimetic peptides may be labelled by being coupled to radioisotopes or colorimetric molecules by conventional methods ("Guide to Protein Purification" Murray P. Deutscher (ed) *Methods in Enzymology* Vol. 182 (1990) Academic Press, Inc. San Diego) and used in both in vivo and in vitro assays to bind to the $\delta$ receptor. Examples of radioisotopes include, but are not limited to, tritium ($^3H$) and carbon-14($^{14}C$) . Examples of colorimetric molecules include, but are not limited to, fluorescent molecules such as fluorescamine, or rhodamine or other colorimetric molecules. By way of example, the peptides coupled to such molecules are useful in studies involving in vivo or in vitro metabolism of the $\delta$ receptor.

The peptide of this invention may also have therapeutic and pharmacologic applications. Pharmaceutically acceptable salts of these peptides may be formulated by reacting the peptide with an acid. While it is possible for the peptides to be administered in a pure or a substantially homogeneous form, it is preferable to present it as a pharmaceutical composition, formulation or preparation.

The formulations of the present invention comprise a peptide as described above, together with one or more pharmaceutically acceptable carriers and, optimally, other therapeutic ingredients. The carrier(s) must be compatible with other ingredients of the formulation and not deleterious to the recipient thereof. The formulations may be conveniently presented in unit dosage form and may be prepared by any method well-known in the pharmaceutical art.

All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous intramuscular, subcutaneous, or intraperitoneal administration conveniently comprise sterile aqueous solutions of the active ingredient with solutions which are preferably isotonic with the blood of the recipient. Such formulations may be conveniently prepared by dissolving the solid active ingredient in water containing physiologically compatible substances such as isotonic sodium chloride (i.e., 0.9% saline), glycine, and the like, and having a buffered pH compatible with physiological conditions to produce an aqueous solution, and rendering the solution sterile. These may be present in unit or multi-dose containers, for example, sealed ampoules or vials.

The formulations of the present invention may incorporate a stabilizer. Illustrative stabilizers are polyethylene glycol, proteins, saccharides, amino acids, inorganic acids, and organic acids which may be used either independently or as admixtures. These stabilizers are preferably incorporated in an amount of 0.10–10.000 parts by weight per part by weight of peptide. If two or more stabilizers are to be used, their total amount is preferably within the range specified above. These stabilizers are used in aqueous solutions at the appropriate concentration and pH. The specific osmotic pressure of such aqueous solutions is generally in the range of 0.1–3.0 osmoles, preferably in the range of 0.8–1.2. The pH of the aqueous solution is adjusted to be within the range of 5.0–9.0, preferably within the range of 6–8. In formulating the peptides of the present invention, anti-adsorption agents may be used.

Additional pharmaceutical methods may be employed to control the duration of action. Controlled release preparations may be achieved by using polymers to complex or absorb the proteins or their derivatives. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the peptides and analogues thereof into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly (methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc magnesium stearate, crystalline cellulose, methyl cellulose, carboxymethyl cellulose, glycerin, sodium alginate or gum arabic among others.

The novel peptides of this invention include those which function as agonists, antagonists, partial agonist or partial antagonist activity in mammals. Those peptides which function as antagonists may be pharmacologically and therapeutically useful where agonists have been used in the prior art, including treatment for opiate or alcohol addition in mammals, preferably humans. Those peptides which function as agonists can be used pharmacologically and therapeutically where agonist have been used in the prior art, such as in the management of chronic pain and post-operative pain in mammals, particularly humans. The therapeutically useful dosage of the peptide used in opiate therapy, alcohol abuse treatments and management of chronic pain and post-operative pain will vary depending on the seriousness of the condition, the time the individual has been afflicted with the condition, the weight of the individual, efficacy of the peptide and other parameters known to one skilled in the art. Based on such parameters the treating physician will determine the therapeutically effective amount of the peptide to be used for a given individual. Such therapies may be administered as often as necessary and for the period of time judged necessary by the treating physician.

The present invention also provides a method of treating mammals, preferably humans, afflicted with a disease or syndrome which comprises the step of administering to the individual a therapeutically effective amount of the peptide or peptides in a pharmaceutically acceptable composition as described above. Administration of the pharmaceutical composition may be for either a prophylactic or therapeutic use. When provided prophylactically, the peptide is provided in advance of any symptom due to the disease or syndrome afflicting the individual. When provided therapeutically, the peptide is provided at (or shortly after) the onset of any symptoms of the disease. The therapeutic administration of the peptide serves to attenuate the disease. Examples of diseases or conditions that can be treated by this method include, but are not limited to, neurological diseases, psychologically defined abnormalities triggered by neuropeptide or neurotransmitter imbalance, brain injury, neurological dysfunctions and other neurological syndromes. Veterinary uses are also intended to be encompassed by this definition.

The therapeutically effective amount of the peptide to be used in the aforementioned treatments will vary depending on the seriousness of the disease, disorder or pain, and the relative efficacy of the peptide. One of skill in the art will know the parameters to evaluate the response of the patient to the peptide and establish the dosage based on those parameters.

All books articles or patents referenced herein are incorporated by reference. The following examples illustrate various aspects of the invention but are in no way intended to limit the scope thereof.

EXAMPLE 1

Synthesis and Characterization of the Ultraselective Opioidmimetic Dipeptides, Tripeptides and Cyclic Peptides

Materials and Methods

2',6'-Dimethyl-L-tyrosine was a gift from John H. Dygos (G. D. Searle and Co.) synthesized by an asymmetric method (44). N$^\alpha$Fmoc-L- and D-Tic were purchased from Advanced ChemTech (Lexington, Ky.). Fmoc-PAL-PEG-PS and Millipore (Waltham, Mass.) were obtained from Millipore (Waltham, Mass.). [$^3$H]DPDPE was a product of NEN-Dupont (Billirica, Mass.) and [$^3$H]DAGO was produced by Amersham (Arlington Heights, Ill.).

Solid Phase Peptide Synthesis

Dipeptide amides were synthesized by solid phase methods using Fmoc-PAL-PEG-PS resin (0.18 mmol/g, 0.09 mmol, Millipore) and Fmoc-Ala-PEG-PS (0.13 mmol/g, 0.065 mmol). NaFmoc-Ala-OH and NaFmoc-Tic-OH were used in the coupling reactions while Dmt was protected as NaBoc-Dmt-OH as reported by Chandrakumar et al. (45). Amino acids were coupled for 1 hour in 4-fold excess diisopropylcarbodiimide (DIPI) in the presence of 4-fold excess 1-hydroxybenzotriazole (HOBt). In the Dmt-Tic acylation step, double coupling was required; the acylating agent employed, PyBrop, occurred in the presence of 4-fold excess N-methylmorpholine (NMM). All peptides were prepared in a Milligen 9050 synthesizer and crude deprotected peptides (88% trifluoroacetic acid, TFA, 5% water and 7% triethylsilane) were purified by preparative HPLC.

Tyr-Tic (control) peptides (Table II) were obtained under the same conditions except that Boc-Tyr(OtBu)-OH was used instead of Boc-Dmt-OH. The synthesis of several analogues (13, 15, 19, 20, 22) was preperformed as described in Temussi et al. (39).

Solution Synthesis of Peptides

Dipeptide acids were prepared by condensing Boc-Dmt-OH and H-L-Tic-OH or H-D-Tic-OH, previously obtained by esterification of Z-L- or D-Tic-OH with isobutylene, as reported (46) and deprotected by catalytic dehydrogenation.

Cyclic dipeptides were preferentially obtained by arrangement in acetone of the dipeptides H-Dmt-Tic-OMe and H-Dmt-D-Tic-OMe (produced by the condensation of Boc-Dmt-OH and Tic-OMe, HCl as given above) at room temperature for 12 hours. The same cyclic dipeptides were also obtained from linear dipeptide amides.

The dipeptide alcohol (compound 5, Table I) was prepared by condensing Boc-Dmt-OH and Tic-CH$_2$OH as given above, while 3-(hydroxymethyl)-3,4-dihydroisoquinoline (H-Tic-CH$_2$OH) was synthesized according to Yamaguchi et al. (47).

In the purification of the peptide products, the Boc group was removed with 95% TFA and the crude peptides purified by preparative HPLC. Homogeneity of all the purified products was assessed by thin-layer chromatography (TLC), analytical HPLC, $^1$H-NMR and electrospray-mass spectrometry (infra vide).

Analytical Determinations

Melting points were determined on a Kofler apparatus and are uncorrected. Optical rotations used a Perkin-Elmer 241 polarimeter with a 10 cm water-jacketed cell.

Peptides for $^1$H-NMR were dissolved in 0.5 mL 90:10 (v/v) DMSO:d6/H$_2$O cryoprotective mixture to give 1 mM solutions. The $^1$H-NMR spectra were run at 400 MHz on a Bruker AMX-500 instrument equipped with an Aspect 3000 computer and at 500 MHz on a Bruker AMX-500 coupled to an X-32 computer. One dimensional $^1$H-NMR spectra were recorded in the Fourier mode with quadrature detection and the water signal suppressed by a low-power selective irradiation in the homogenate mode.

The determination of mass ions, was conducted using a triple stage quadruple mass spectrometer (TSQ 700, Finnigan MAT, San Jose, Calif.). A pneumatically assisted electrospray (ion spray) interface was used for sample introduction into the atmospheric ionization source of the mass spectrometer. The interface capillary sprayer was operated at a positive potential of 4.5 kV. Ionized analyte was then transferred from atmospheric pressure to a vacuum ($1.5 \times 10^{-8}$ Torr) through a heated metal capillary held at 200° C. Multiple charged molecular ions of the type $M^{+n}H^{n+}$ exiting the capillary were focused by a tube lens through a skimmer and then focused by an octapole lens into the mass analyzer. Samples were analyzed by direct infusion using a syringe pump (Harvard Apparatus, Mass.) at a flow rate of 3 µL/min. Concentrations of peptide samples were typically 50 pmol/µL water-methanol (50:50, v/v) containing 1% acetic acid. Full scan MS experiments were obtained by scanning quadruple 1 from m/z 200 to 1500 in 3 sec. Data were transferred to a DEC workstation 5000/125 computer (Digital Equipment Company, Maynard, Mass.) and processed using the deconvolution software package Biomass (Finnigan MAT) in order to acquire the molecular weight determinations from the multiplicity of charged ion envelopes.

Preparative reverse-phase HPLC was carried out using a Waters Delta Prep 3000 Å (30×0.3 cm, 15 µm particle size) column. The peptides were eluted with a gradient of 0% to 60% B over 25 min. at a flow rate of 30 mL/min. using mobile phases A (10%, v/v, acetonitrile in 0.1% TFA) and B (60%, v/v, acetonitrile in 0.1% TFA). Analytical HPLC analyses were performed on a Bruker liquid chromatography LC-21 instrument using a Waters Pico-Tag C18 column (150×3.9 mm, 5 µm particle size) and equipped with a Bruker LC 313 UV variable wavelength detector. Recording and quantification were accomplished with a chromatographic data processor coupled to an Epson computer system (QX-10). Analytical determinations and capacity factor (K') of the peptides were determined using HPLC conditions in the above solvent systems in a linear gradient from 0% to 100% B in 25 min at a flow rate of 1 mL/min. All analogues showed less than 1% impurities when monitored at 220 nm.

TLC used precoated plates of silica gel F254 (Merck, Darmstadt, Germany) in the following solvent systems: (A) 1-butanol/HOAc/$H_2O$ (3:1:1); (B) EtOAc/pyridine/HOAc/$H_2O$ (6:2:0.6:1.1); (C) $CHCl_3$/benzene/methanol (17:1:2). Ninhydrin (1%, Merck), fluorescamine (Hoffman-La Roche) and chlorine reagent were used as detection sprays. A compilation of the analytical properties of the peptides are listed in Tables I and II.

Receptor Binding Analyses

Rat membrane synaptosome preparations ($P_2$ fraction) were prepared as detailed previously, which included a preincubation step to reduce the presence of endogenous ligands and binding of G proteins (33,40). The δ and µ receptor sites were labeled with [$^3$H]DPDPE (34.3 Ci/mmol) and [$^3$H]DAGO (60.0 Ci/mmol), respectively, under equilibrium conditions (2 hr at 22°–23° C.). Samples were rapidly filtered through wetted glass fiber filters and thoroughly washed with 6 mL (3×2 mL) ice-cold 50 mM Tris-HCl, pH 7.5, containing 0.01–0.1% chicken egg albumin or bovine serum albumin. Each peptide was assayed in duplicate with 5–9 dosages using 3–4 synaptosomal preparations. The filters were dried at 70° C. and the radioactivity determined after an overnight incubation period in CytoScint to maximize the radioactivity detected and reduce variability between samples. The $IC_{50}$ values were converted to affinity constants ($K_i$) according to Cheng and Prusoff (48). The mean and standard error of the mean of repetitions (n) are listed in Tables III and IV.

Multi-site binding analyses, based on stringent statistical methods, were performed as described in Bryant et al. (41) and Attila et al. (49). Receptor assays were conducted in triplicate with 25–35 graded concentrations of peptide; the resulting curves were both individually assessed and combined from several distinct assays, and analyzed using Prism™ (v. 1.02, GraphPad, San Diego, Calif.). A two-site binding model was considered valid only with Hill Coefficients ($\eta$)<0.850 and narrow 95% confidence intervals with $P<0.0001$ for the F test between one- and two site fits (41,49).

Bioassays

The in vitro pharmacological assays were undertaken using published methods (32) based on the organ bath technique of Kosterlitz and Watt (50). For µ receptors, a 2–3 cm segment of guinea-pig ileum (GPI) mounted in a 20 mL organ bath and for δ receptors, a single mouse vas deferens (MVD) was obtained from a mature animal. Each peptide in 10–100 µL Krebs solution was tested for agonist activity by the inhibition of electrically stimulated contractions in comparison to dermorphin (H-Tyr-D-Ala-Phe-Gly-Tyr-Pro-Ser-$NH_2$), a µ receptor agonist, and through the effects of deltorphin C (H-Tyr-D-Ala-Phe-Asp-Val-Val-Gly-$NH_2$), a $\delta_1$ receptor agonist, and compared against naltrindole, a $\delta_1$ receptor antagonist. Dose response curves were obtained in the absence and presence of multiple concentrations of antagonists and $pA_2$ (the negative logarithm of the concentration to cause 50% inhibition) calculated according to Schild (51). For active compounds the range of peptides used in this assay fell between 0.1 nM to 100 nM, whereas those compounds with minimal response were tested at concentrations as high as 10 µM or greater.

Analgesia

Animal procedures were conducted under protocols approved by the Animal Use and Care Committee, NIEHS, an AALAC accredited facility. Tail flick test (TFT) used a radiant heat source on the tail of Fisher 344 rats or CD-1 mice (52). The response was standardized by the subcutaneous (sc) injection of 5 mg morphine sulfate/kilogram (Kg) body weight or 0.1–0.25 mg morphine/Kg body weight by iv injection; peptides were injected in 100 µL volume in sterile saline. Central mediation of analgesia (agonist action) was determined from the direct administration of the peptide intra-cerebro-ventricular (icv) in rats, intravenous (iv) in rats and mice, and sc and intrathecal in mice; antagonist activity is the reduction of analgesia induced by morphine sulfate or naltrindole and related compounds or vice versa. Intrathecal injection of peptides in mice used the method of Hylden and Wilcox (53). A base-line and cut-off 10 sec were determined in the TFT with naive and morphine-dosed animals, respectively, to prevent damage to the tail. 1 µg to 10 mg per kilogram of animal was used for iv, icv or sc; higher doses in the mg range were used for sc injection.

Dmt-Tic-OH (peptide 1) at a dose of 100 ug/mouse (iv administration) produced no demonstrable analgesia by the tail flick test, it completely blocked the effect of 0.25 mg/kg morphine injected iv in keeping with the antagnostic action observed in vitro (Table VI).

Molecular Dynamics Simulations

Molecular dynamics (MD) simulations were performed using AMBER (v. 3.0, Rev. A) (54) on a Silicon Graphics Indigo$^2$ computer system. AMBER output was visualized and analyzed using MULTI (v. 3.0.0) (54) and conformational searches were performed using MacroModel (v.4.0) (55). Dmt-Tic-OH, Tyr-Tic-OH and c(Dmt-Tic) were solvated in TIP3P (Monte Carlo) water molecules under periodic boundary conditions. Minimizations involved constant volume, while MD embraced constant pressure. Both procedures included constant temperature (300K), constant dielectric ($\epsilon=1$), a step size of 0.001 ps, and 9 Å non-bonded cutoffs.

High energy contacts produced by unfavorably arranged solvent were reduced through minimization before and after MD on the solvent only. Minimizations lasted 500 cycles using steepest descent algorithm for the first 100 steps, conjugate gradient for the last 400 steps, and stopping with rms gradient of 0.10 Kcal/mol-Å. MD were performed on the solvent for 20 ps; 4 MD runs with 1,000 steps/run. Solvent and solute were minimized for 200 cycles using the same method as above. MD simulations of the solvated peptides were performed for 100 ps; 100 MD runs with 1,000 steps/run. MD coordinates were output every 100 steps and the pairlist updated every 20 ps.

Monte Carlo conformational searches incorporated three unique starting structures for each dipeptide. Analysis of the starting structures proceeded by 1000 steps of variable torsion searching with values ranging from 0°–360° for each of the eight rotatable dihedrals and all combinations of the values were formulated to generate structures that were compliant with the nonbonded contacts, chirality, and ring closure constraints. A conformer was considered unique if it's energy was within 20 kJ/mol of the lowest minimum found during the search and if it did not duplicate any previously stored structures. All conformations generated during the search were minimized in the AMBER force field using the conjugate gradient algorithm stopping the rms gradient of 0.01 kJ/mol-Å.

The unique opioidmimetic compounds containing 2',6'-dimethyl-L-tyrosine (Dmt) exhibited high $\delta$ affinity, two of which had extraordinarily high selectivities for $\delta$ opioid receptors (Table III), and were several orders of magnitude greater than that of the Tyr-Tic peptides (Table IV). An interesting correspondence appeared between the receptor binding, the goodness of fit to one-or two-binding site models for the $\delta$ receptor, and the three dimensional architecture.

Receptor Binding Analyses

Explicit alterations in opioid receptor binding affinities occurred with the replacement of Tyr[1] by Dmt in Tic[2]-containing peptides (Tables III and IV) as follows: (i) A large increase in $\delta$ affinity in all Dmt analogues (Table III) in comparison to the Tyr-Tic peptides (Table IV); e.g., Dmt-Tic-OH (peptide 1, Table III) had a 8,500-fold higher $\delta$ affinity and 1,000-fold greater selectivity than Tyr-Tic-OH (peptide 12, Table IV). (ii) The profile of $\delta$ affinities and selectivities for the Dmt-Tic dipeptides (peptides 1–5) and the Dmt-Tic-Ala tripeptides (peptides 8–11) were qualitatively identical. (iii) Elimination of the anionic charge of the C-terminal carboxyl function either by amidation or reduction to a hydroxymethyl group exerted marginal effects on $\delta$ affinity; on the other hand, $\mu$ affinity substantially increased to concomitantly reduce $\delta$ selectivity of the Dmt-Tic peptides (Table III), a phenomenon not observed with the Tyr-Tic peptides (Table IV). (iv) Substitution of the D-stereoisomer for L-Tic simultaneously reduced $\delta$ affinity and enhanced $\mu$ affinity, particularly in the aminated peptides, and resulted in a reversal of selectivity ($\delta \rightarrow \mu$) in analogues peptide 4, peptide 10 peptide 11, peptide 15 and peptide 22. (v) Cyclic(Dmt-Tic) (peptide 6) retained significant $\delta$ affinity, which represented a 4,000-fold increase relative to c(Tyr-Tic) (peptide 17); the presence of D-Tic in the cyclic analogue substantially abolished both $\delta$ receptor recognition and selectivity (see peptide 7).

Binding site analyses (Table V) revealed that the Dmt-Tic-OH (peptide 1) and Dmt-Tic-NH$_2$ (peptide 2), in comparison to Dmt-Tic—CH$_2$OH (peptide 5), c(Dmt-Tic) (peptide 6) as well as the Dmt-Tic-Ala tripeptides (peptides 8 and 9) could be fitted to distinctly different $\delta$ receptor subsites. The Hill Coefficient ($\eta$) for Dmt-Tic-OH (peptide 1) Dmt-Tic-NH$_2$ (2) were 0.939 and 0.987, respectively, indicative of fitting a one-site binding model. However, Dmt-Tic—CH$_2$OH (peptide 5) and the constrained dipeptide c(Dmt-Tic) (peptide 6) exhibited good fits for the two-site model in which $\eta$ equalled 0.777 and 0.725, respectively; similarly, the tripeptides Dmt-Tic-Ala-OH (peptide 8) ($\eta=0.708$) and Dmt-Tic-NH$_2$ (peptide 9) ($\eta=0.801$) also revealed a better fit for a two-site receptor binding model. All these values were highly significant with $P<0.0001$ and narrow 95% confidence intervals (Table V).

Biological Activity

In the MVD assay, Dmt-Tic-Ala-OH (peptide 8) produced antagonism with a pA$_2$=8.4 (4 nM) against deltorphin C as the agonist (Table VI). This compares favorably with naltrindole with a pA$_2$=9.2 (0.7 nM). No activity (>10 µM) was recorded for µ receptors using guinea-pig ileum with Dmt-Tic-Ala-OH (peptide 8), while naltrindole had a pA$_2$=7.3 (53 nM) which indicated a loss of specific preference for $\delta$ bioactive sites in contrast to the extraordinary high selectivity of peptide 8. Peptides 1, 2, 5, 6 and 9 also exhibited antagonist properties (Table VI).

A preliminary screening on sc injection of 100 µg peptide 8 (Dmt-Tic-Ala-OH) per mouse produced significant analgesia in the TFT ($P<0.05$). Post-injection of peptide to morphine treated rats failed to reverse the analgesic effect of morphine; similarly, peptide treated mice were ineffective in preventing a morphine challenge.

Molecular Dynamics

Monte Carlo conformational searching and AMBER molecular dynamics were applied to Tyr-Tic-OH, Dmt-Tic-OH and c(Dmt-Tic) in order to isolate the unique and most stable, low energy conformers of these dipeptides in water. With only eight rotatable dihedrals (defined as the angle of four atoms) and only two rotatable backbone dihedrals, the conformational possibilities were sampled exhaustively and the unique conformations were minimized. The lowest potential energies reported (Table VII) were used to indicate the most stable combinations of dihedrals for these dipeptides. The structural differences, in addition to the unique affinities and selectivities at the $\delta$ receptor sites, implicate tertiary architectures that could represent bioactive conformations.

Among the 3,000 low energy structures generated from the Monte Carlo searches of Tyr-Tic-OH, three clusters of unique low energy conformations were evaluated. Cluster I contained 151 conformers with energies of −158.4 kJ/mol (Table VII). The aromatic rings of Tyr and Tic occupied parallel planes, but the atoms of each cyclic structure were not aligned. The backbone atoms resided in a plane that was perpendicular to the plane of the aromatic rings and the distance between the two rings was approximately 3.8 Å to 4.0 Å. The second cluster consisted of 92 conformers with energies of −146.9 kJ/mol. The aromatic rings existed in planes that were not quite perpendicular as a result of the change of $\chi_2$ at Tyr, rendering a distance of 6.5 Å to 7.5 Å. Additionally, Tyr was oriented in a plane that was approximately 60° relative to the plane circumscribed by the backbone atoms. The Tyr aromatic ring in the third cluster was positioned almost 10 Å from the Tic aromatic ring and was virtually oriented 180° relative to the backbone plane.

The conformers of Dmt-Tic-OH found in cluster I (Table VII) exhibited similar orientations as found for cluster I of Tyr-Tic-OH: the aromatic rings were parallel to each other and about 3.8 Å to 4.0 Å apart. Cluster II orientations were similar to those of cluster I despite the changes at $\chi_2$ of Tic. The third cluster differs from the previous ones only with respect to the carbonyl and —OH groups at the C-terminus which were situated below the planes of the other backbone atoms; the aromatic rings were located 4.3 Å to 5.0 Å apart. Cluster IV exhibited unusual changes in $\phi$ and $\chi_1$ dihedrals of Tic which imparted a distance of 6.5 $\chi$ to 7.0 $\chi$ between Tic and Dmt. In contrast to $\chi_2$ of Tyr in Tyr-Tic-OH, the methyl groups of Dmt of Dmt-Tic-OH limited rotation around the $\chi_2$ torsions of Dmt thereby resulting in a parallel orientation of the aromatic rings that was observed in all the low energy clusters of this dipeptide.

In spite of the imposed cyclization in the backbone of c(Dmt-Tic), the aromatic rings maintained a parallel orientation to each other. However, the ring of Dmt was aligned with the saturated alkane (lower) ring of Tic instead of the aromatic (upper) ring; this contrasts with the low energy clusters of both Tyr-Tic-OH and Dmt-Tic-OH. The $\alpha$ carbon distance of this "tricyclic" peptide was significantly shorter (2.9 Å) than the average distance normally observed (3.8 Å) between $\alpha$ carbons in peptides in general.

The conclusion that can be drawn from these molecular dynamics conformational studies is that the orientation of the aromatic rings of Dmt and Tic, which occupy planes with parallel alignment to each, is required to achieve an optimal conformation for bioactivity. The essentiality of the presence of two methyl groups on Tyr (Dmt residue) becomes readily apparent in that it forces the nominally freely rotatable Tyr into a strict spatial orientation and proper alignment. This argument is further strengthened by the model of c(Dmt-Tic), a peptide which lacks the cationic charge of the N-terminal amide yet interacts with $\alpha$ receptors presumably due to the parallel alignment of its Dmt and Tic rings. However, as noted above, the spatial displacement between the ring systems could account for the intermediate value in and discrepancy between $\delta$ affinities observed among c(Dmt-Tic), Dmt-Tic-OH (Table III) and that of Tyr-Tic-OH (Table IV).

Discussion

These novel opioidmimetics represent the smallest known compounds that interact with the $\delta$ opioid receptor with extremely high specificity affinity and selectivity. Their receptor selectivity surpasses those of previously known opioid peptides and non-peptides by several hundred-fold; e.g., the di- and tripeptides containing the Tyr-Tic moiety (39), the tri- and tetrapseudopeptides of Schiller et al. (37,38), the deltorphins (33,40,41), a Dmt-D-Ala-arylalkylamide dipeptide which is weakly µ selective (45, 56), linear and cyclic enkephalin (1,2), cyclic dermorphin-(30) or deltorphin-derived analogues (31,57), and the naltrexone-derived non-peptide opioid antagonists (58,59). The c(Dmt-Tic) represents the first $\delta$ selective opioid peptide lacking an amine group at the N- terminus. In addition its cyclic information provides enhanced stability and its small size may allow it to pass through the blood brain barrier. Its selectivity is comparable to other of opioid peptides (1,2) and non-peptide opiates (58,59). These peptides therefore question the conventionally maintained requirement of a N-terminal amine, the role of message and address domains (58,60), and the necessity of the aromatic phenylalanine residue in positions 3 or 4 (37,38,58,59) to bind to the $\delta$ receptor.

The receptor binding data establishes that 2',6'-dimethylation of Tyr enhances the interaction of the peptide at the binding site more than the addition of a single methyl group in a constrained peptide (61). Whereas a free acid function or amide group at the C-terminus marginally effects $\delta$ affinity, the loss of the carboxylate ion increases interaction with the µ receptor as previously noted with deltorphin A heptapeptide analogues (42). Without being bound by theory, presumably the carboxylate anion forms a salt bridge with a cation in the $\delta$ receptor (62, 84), providing evidence that the µ receptor lacks a complimentary cation site; alternately, the µ receptor may contain an anionic function that would partially repel binding of the incoming ligand. Furthermore, the change in chirality from L- to D-Tic which abolishes high $\delta$ affinity while simultaneously enhancing µ affinity (yielding peptides with reduced $\delta$ selectivity or the acquisition of µ selectivity). This is similar to changes in affinity and selectivity observed with isomeric modifications in TIPP tetrapeptides (37), dermorphin (63, 93) and deltorphin A (33). This suggests that a correct and decisive stereoconfiguration is essential for recognition by $\delta$ receptors and that the spatial displacement of the C-terminal group imposed by the D-isomer enhances binding at µ sites.

The incorporation of unnatural bicyclic constrained amino acids at the N-terminal region of opioid peptides were implemented to reduce conformational flexibility, restrain secondary structure, and determine the influence of the benzyl side-chain of Phe on activity (31,32). Substitution of Tic, among other bicyclic residues, for Phe at position 3 in the $\delta$ selective opioid deltorphin C (32,57) significantly reduced receptor binding properties. Incorporation of Tic into somatostatin, a non-opioid peptide whose analogues evoke an opioid response based on the early observations of Terenius (64)) produced µ antagonism (65). The cyclic tetrapeptide analogues derived from deltorphin B (H-Tyr-D-Ala-Phe-Glu-Val-Val-Gly-NH$_2$), in which Phe[3] was replaced by Tic developed analogues with distinct properties for µ receptors (31) comparable to those of [Tic[2]]dermorphin (93) [Tic[3]]dermorphin (63).

Modifications of opioid activity that focused on alterations at the crucial N-terminal Tyr residue through use of various conformationally constrained enkephalin analogues or analogues based on the N-terminal dermorphin/deltorphin sequence, Tyr-D-Xaa-Phe (30,61,66) resulted in the $\delta$ selectivities that were relatively modest ($K_i^{\mu}/K_i^{\delta}$=100–600) and $\delta$ affinities in the low nM range (30,61). Another series of analogues in which the aromatic ring of Tyr was directly modified by the single substitution of a methyl group at ring position 2' (61) or disubstitution at positions 2' and 6' (45,54,66–68). The former analogue, [2'-Me-Tyr[1]]DPDPE, exhibited relatively high $\delta$ affinity and $\delta$ selectivity (61), and incorporation of Dmt into the same DPDPE analogues produced weakly $\delta$ selective (69) to non-selective opioid peptides (67). On the other hand, [Tmt[1]]deltorphin B [Tmt= (2S,3S)-β-methyl-2'-6'-dimethyltyrosine, which contains a third methyl group on the β carbon of Dmt], [Dmt[1]] Deltorphin B, however, maintained high $\delta$ affinity but dramatically lost $\delta$ selectivity due to the acquisition of high µ affinity; nonetheless, the analogue fitted a two-site binding model (n=0.792±0.030; F=18.8. P<0.001 and df 2;91) for δ receptors identical to the parent peptide (Salvadori et al., unpublished observations). Interestingly, the dipeptide Dmt-D-Ala-arylalkylamide was μ selective (45,56). The presence of Dmt in these peptides conferred analgesia in vivo in relation to the control compounds (45,56,68,69); the efficacy of subcutaneously administered peptide was, however, one tenth that of morphine (69). The novel peptide Dmt-Tic-Ala-OH (peptide 8) similarly produced analgesia in mice.

Existing models and hypotheses for opioid peptide interaction with opioid receptors were an initial outgrowth of detailed studies with active enantiomers of opiate narcotics. In particular, the N-terminal tyrosine moiety (71–75) and Phe at position 4 of enkephalin (73,75) or $Phe^3$ of the dermorphin/deltorphin opioid peptides (3) were considered to structurally overlap with the aromatic phenol ring and piperidine nitrogen of morphine and related opiates (59,76). The cyclic enkephalins (2,77,78) presumably were developed to conformationally constrain the flexible peptides and mimic the rigidity of the narcotic opiates. It was later proposed that opioids contributed hydrophilic- and hydrophobic-attractive forces in the receptor recognition process (20,71,79,80), similar to a mechanism observed with enzymes and antibodies (80–82). Binding at the receptor was considered to occur through hydrophobic interaction with nonpolar sites and ion-pair formation (83), and to an anionic site in the receptor pocket (80). As a modification of this concept, the membrane-assisted receptor selection hypothesis of Schwyzer (84) postulated that the overall charge of the ligand was responsible for selectivity, in which a negative charge was a key feature for δ selectivity while positive charges characterized μ selective opioids. Another proposal, based on the structure of opiate narcotics, led to the hard base-soft base theory (39,62,85) in which the $Tyr^1$ and $Phe^3$ of dermorphin assumes a T-shape in comparison to the rigid structure of fentanyl (62) or phenylpiperidine opiates (80): a hard base ($B_h$, consisting of the amino group of the peptide chain), a soft base ($B_s$, any functional group at the C-terminus), a hydrogen bond donor group (the phenolic moiety of the tyramine side-chain of $Tyr^1$), and an aryl ring adjacent to the hard base (62,85). Another concept was introduced in which bivalent opiates and opioids contain distinct message-address domains (60) based on the model developed for ACTH (86).

The presence of distinct β-turns in the flexible opioid peptides-the mammalian enkephalins (75,76,87), and the amphibian skin-derived dermorphins (88) and deltorphins (20,41,43,79,89,90)-contribute to an optimum peptide conformation between the two pharmacophores, $Tyr^1$ and $Phe^3$ in dermorphins/deltorphins (32,33,88) or $Phe^4$ in constrained enkephalins. Tertiary peptide conformation is the central aspect in binding to and differentiation among binding subsites or receptor subtypes (41,43). Additional β-turns in the region C-terminal to $Phe^3$ (89) may also assist in positioning of specific hydrophobic residues within the C-terminal region for better accessibility within the receptor binding site (22,26,27,34–36) or producing distinct variations in molecular architecture (41).

With the recent discovery that the simple dipeptide Tyr-Tic-$NH_2$ exhibited opioid activity (39) (Table II), we are left with a dilemma of how to interpret the high δ affinity and ultraselectivity of peptides that lack an aromatic residue at position 3, such as seen in Dmt-Tic-OH, Dmt-Tic-Ala-OH and c(Dmt-Tic), in light of the antecedent postulates. A low energy model of Tyr-Tic-$NH_2$ indicated that nearly a 90° angle was acquired between the aromatic rings comparable to that in N-methylnaltrindole (39)and supports the antagonism of [L-$Tic^2$]-peptides. Our molecular dynamics analysis of Tyr-Tic-OH, Dmt-Tic-OH and c(Dmt-Tic) further revealed distinct conformational differences (supra vide). Without being bound by theory the consolidation of a strong hydrophobic character instituted by the additional pair of methyl groups on the aromatic ring of Tyr in the di-and tripeptides containing L-$Tic^2$ indicates that hydrophobicity also contributes to anchoring the peptide in the receptor pocket. As suggested from studies on morphine analgesics (62,83) and dermorphin (91), hydrophobic interactions with nonpolar sites in the receptor might occur with the aromatic rings of $Dmt^1$ and $Tic^2$, which may be important elements in controlling the affinity of the ligand at the binding site. Nonetheless, peptide conformation may be a crucial factor in allowing optimal binding within the receptor "pocket."

The cationic amine and hydroxyl groups of the first residue play significant roles in securing or stabilizing the peptide within the receptor through a combination of hydrogen bonding and formation of a salt bridge with an anionic site (80). The N-terminal amine is essential for activity since binding is lost by acetylation (2). The Tyr hydroxyl group is an important auxiliary function in flexible opioids, since substitution with $Phe^1$ (2) and non-aromatic ring compounds (30) reduce binding to opioid receptors, however, it should be noted that neither fentanyl nor other opiates contain hydroxyl groups (62). The presence of a ionizable anion at the C-terminus simultaneously confers high affinity binding to δ sites and repulsion from the μ receptor (Table III) (21). It is conceivable that the inherently higher flexibility of the tripeptide would permit interaction of the acid function of C-terminal $Ala^3$ in Dmt-Tic-Ala-OH with a cationic site comparable to the Dmt-Tic-OH dipeptide.

Figure 1A:
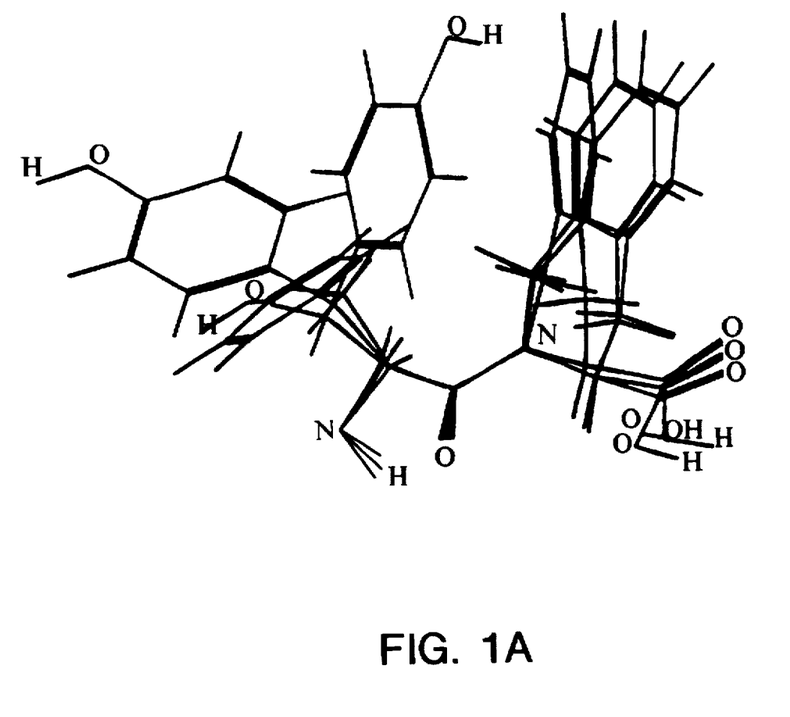
Figure 1B:
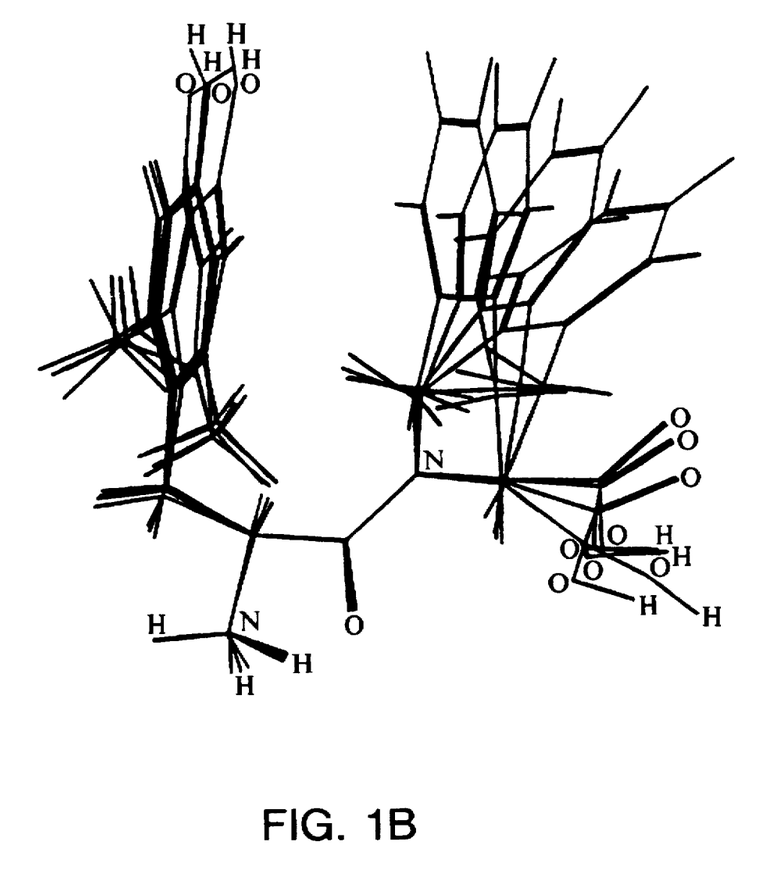
Figure 1C:
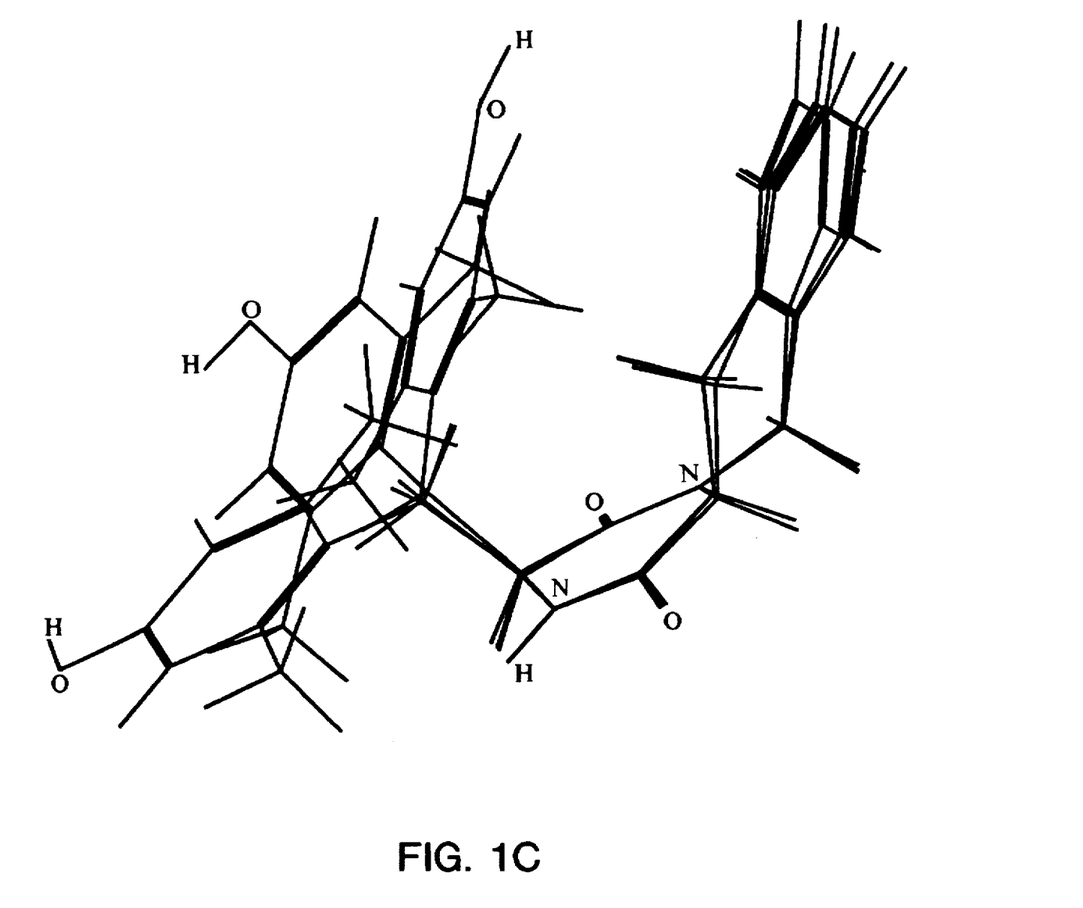

The cyclized structure formed by a peptide bond between the N- and C-termini of Dmt-Tic represents the first fully active opioid lacking a N-terminal amino anion function that exhibits a δ affinity comparable to DPDPE and the selectivity of [$Dmt^1$]DPDPE (69). These results support the involvement of hydrophobic forces, in addition to hydrogen bonding, a carboxylate anion and protonated amine nitrogen in receptor recognition. In comparison to the inactive c(Tyr-Tic), the association of c(Dmt-Tic) with δ receptors is promoted by the increase in hydrophobicity of Dmt and peptide conformation induced by the methyl groups. These methyl groups may contribute to an enhanced stabilization at either the receptor site by the overall hydrophobicity and spatial requirements due to the additional bulky groups, thereby resulting in a profound effect on the positioning of the hydroxyl group in an environment that favors hydrogen bonding in the receptor pocket. The aromatic rings obviously contribute to the binding mechanism by formation of water-excluding hydrophobic interactions at the lipophilic environment in the trans-membrane spanning regions of the receptor protein (94). Furthermore, Dmt and Tic could enhance the overall hydrophobicity associated with the peptide or spatially stabilize the ring within the receptor in conjunction with the methyl groups. A further observation on the conformation of c(Dmt-Tic) is the formation of an apparent third 5-membered ring associated with Tic and that it appears to be more similar to Dmt-Tic-OH than Tyr-Tic-OH (FIG. 1).

The present invention has been described in some detail by way of illustrations and examples for the purpose of clarity of understanding. It will be obvious that certain changes and modifications may be practiced within the scope of the appended claims.

TABLE I

Analytical Characterization of the Dmt-Tic Peptides

| Peptide | R | R' | $R_f$ A | B | K' | (M + H)+ |
|---|---|---|---|---|---|---|
| 1. Dmt-Tic | | OH | 0.66 | 0.23 | 5.83 | 368 |
| 2. Dmt-Tic | | NH$_2$ | 0.69 | 0.43 | 6.32 | 367 |
| 3. Dmt-D-Tic | | OH | 0.61 | 0.16 | 5.83 | 368 |
| 4. Dmt-D-Tic | | NH$_2$ | 0.64 | 0.45 | 0.45 | 367 |
| 5. Dmt-Tic | | CH$_2$OH | 0.67 | 0.51 | 7.27 | 354 |
| 6. c(Dmt-Tic) | | | 0.95 | 0.89 | 10.4 | 350 |
| 7. c(Dmt-D-Tic) | | | 0.91 | 0.88 | 8.21 | 350 |
| 8. Dmt-Tic | Ala | OH | 0.73 | 0.26 | 8.68 | 440 |
| 9. Dmt-Tic | Ala | NH$_2$ | 0.67 | 0.43 | 9.31 | 439 |
| 10. Dmt-D-Tic | Ala | OH | 0.64 | 0.27 | 6.78 | 440 |
| 11. Dmt-D-Tic | Ala | NH$_2$ | 0.66 | 0.41 | 8.81 | 439 |

Table Legend for FIG. I. Analytical Characterization of the Dmt-Tic Peptides. The $R_f$ values, capacity factor (K') and molecular weight of the peptides.

TABLE II

Analytical Characterization of the Tyr-Tic Peptides

| Peptide | R | R' | $R_f$ A | B | K' | MW |
|---|---|---|---|---|---|---|
| 12. Tyr-Tic | | OH | 0.62 | 0.21 | 3.61 | 340 |
| 14. Tyr-D-Tic | | OH | 0.61 | 0.21 | 3.62 | 340 |
| 16. Tyr-Tic | | CH$_2$OH | 0.66 | 0.45 | 4.23 | 326 |
| 17. c(Tyr-Tic) | | | 0.73 | 0.69 | 5.21 | 322 |
| 18. c(Tyr-D-Tic) | | | 0.85 | 0.81 | 4.57 | 322 |
| 21. Tyr-D-Tic | Ala | OH | 0.63 | 0.19 | 4.24 | 411 |

Table Legend for FIG. II. Analytical Characterization of the Tyr-Tic Peptides. The $R_f$ values, capacity factor (K') and molecular weight of the peptides.

TABLE III

2',6'-Dimethyl-L-Tyrosine-Tic-R-R' Opioidmimetic Peptide Binding Affinities and Receptor Selectivities

| Peptide | R | R' | $K_i$(nM) δ | μ | μ/δ |
|---|---|---|---|---|---|
| Dipeptides | | | | | |
| 1. Dmt-Tic | | OH | 0.0225±0.002 (5) | 3,317±435 (7) | 147,422 |
| 2. Dmt-Tic | | NH$_2$ | 1.22±0.09 (6) | 276.8±26.9 (3) | 227 |
| 3. Dmt-D-Tic | | OH | 13.5±1.59 (4) | 224.4±25.6 (3) | 17 |
| 4. Dmt-D-Tic | | NH$_2$ | 56.9±2.90 (3) | 3.8±0.24 (3) | 0.067 |
| 5. Dmt-Tic | | CH$_2$OH | 0.44±0.14 (6) | 151.4±16.3 (3) | 344 |
| 6. c(Dmt-Tic) | | | 9.58±1.98 (6) | 634.9±69.3 (3) | 66 |
| 7. c(Dmt-D-Tic) | | | 498.7±117 (3) | 728.1±72.9 (3) | 1.5 |
| Tripeptides | | | | | |
| 8. Dmt-Tic | Ala | OH | 0.285±0.03 (6) | 5,813±675 (4) | 20,396 |
| 9. Dmt-Tic | Ala | NH$_2$ | 0.241±0.02 (5) | 47.1±3.4 (4) | 195 |
| 10. Dmt-D-Tic | Ala | OH | 88.7±13.8 (5) | 82.8±2.0 (3) | 0.93 |
| 11. Dmt-D-Tic | Ala | NH$_2$ | 46.4±2.7 (3) | 5.8±0.85 (4) | 0.13 |

Table Legend for FIG. III. 2',6'-Dimethyl-L-Tyrosine-Tic-R-R' Opioidmimetic Peptide Binding Affinities and Receptor Selectivities. Receptor binding assays were conducted as given in the Example 1 with the affinity constants ($K_i$) derived from the graphic determination of IC$_{50}$ and calculated according to Chang and Prusoff (48). The mean ± standard error of mean for n repetitions (in parenthesis) are listed for each peptide.

TABLE IV

Binding Affinities and Selectivities of H-Tyr-Tic-R-R' Control Peptides

| Peptide | R | R' | $K_i$(nM) δ | μ | μ/δ |
|---|---|---|---|---|---|
| Dipeptides | | | | | |
| 12. Tyr-Tic | | OH | 191.7±47.8 (7) | 28,411±2,941 (3) | 148 |
| 13. Tyr-Tic | | NH$_2$ | 165.9±48.1 (4) | 28,712±3,305 (7) | 173[a] |
| 14. Tyr-D-Tic | | OH | 9,046±719 (5) | 26,258±427 (3) | 2.9 |
| 15. Tyr-D-Tic | | NH$_2$ | 5,959±98.1 (4) | 3,135±491 (4) | 0.53[a] |
| 16. Tyr-Tic | | CH$_2$OH | 128.1±34.7 (4) | 11,003±1,851 (3) | 86 |
| 17. c(Tyr-Tic) | | | 41,848±4,814 (3) | 51,474±2,913 (3) | 1.2 |
| 18. c(Tyr-D-Tic) | | | 8,908±4,091 (4) | 127,602±22,860 (3) | 14 |
| Tripeptides | | | | | |
| 19. Tyr-Tic | Ala | OH | 56.1±10.3 (3) | 8,291±1,377 (3) | 148[a] |
| 20. Tyr-Tic | Ala | NH$_2$ | 55.5±13.7 (3) | 33,844±1,405 (3) | 610[a] |
| 21. Tyr-D-Tic | Ala | OH | 2,346±356 (3) | 14,028±2,166 (3) | 6 |
| 22. Tyr-D-Tic | Ala | NH$_2$ | 21,076±4,427 (3) | 8,146±1,377 (3) | 0.39[a] |

Table Legend for FIG. IV. Binding Affinities and Selectivities of H-Tyr-Tic-R-R' Control Peptides. The legend to Table I is applicable to the data listed herein.

[a]Data from Temussi et al. (39).

TABLE V

Hill Coefficients and Statistical Analysis for Goodness-of-fit for One- and Two-Site δ Receptor Binding Models

| Peptide | Hill Coefficient Mean | 95% CI$_{log}$ | Two-site vs. One-site DF | F | P | Percent Low affinity sales | $K_i(nM)^a$ High | Low |
|---|---|---|---|---|---|---|---|---|
| 1. Dmt—Tic—OH | −0.939 ± 0.040 | −1.018 to −0.860 | 2;63 | 1.41 | 0.251 | 30.7 ± 91.5 | 0.022 | — |
| 2. Dmt—Tic—NH$_2$ | −0.987 ± 0.044 | −1.076 to −0.899 | 2;57 | 0.30 | 0.743 | 6.2 ± 40.1 | 1.06 | — |
| 5. Dmt—Tic—CH$_2$OH | −0.728 ± 0.032 | −0.792 to −0.663 | 2;63 | 26.0 | <0.0001 | 20.9 ± 5.3 | 0.13 | 5.2 |
| 6. c(Dmt—Tic) | −0.777 ± 0.040 | −0.856 to −0.697 | 2;68 | 15.5 | <0.0001 | 86.8 ± 3.9 | 0.09 | 9.4 |
| 8. Dmt—Tic—Ala—OH | −0.708 ± 0.036 | −0.781 to −0.636 | 2;72 | 18.9 | <0.0001 | 23.4 ± 6.5 | 0.12 | 4.8 |
| 9. Dmt—Tic—Ala—NH$_2$ | −0.801 ± 0.030 | −0.862 to −0.741 | 2;75 | 19.9 | <0.0001 | 12.6 ± 3.7 | 0.18 | 10.7 |

Table Legend for Figure V. Hill Coefficients and Statistical Analysis for Goodness-of-fit for One- and Two-Site δ Receptor Binding Models. Refer to EXPERIMENTAL PROCEDURES for details for the methods and for validation of the criteria. $^aK_i$ values were derived from the formulas in the fitting of one-site vs two-site binding models in Prism ™ (GraphPad) which are essentially the same as those reported in Table III.

TABLE VI

Bioactivity of 2',6'-Dimethyl-L-Tyrosine Opioidmimetic Peptides

| Peptide | MVD pA$_2$ | MVD nM | GPI pA$_2$ | GPI IC$_{50}$ (μM) |
|---|---|---|---|---|
| 1. Dmt—Tic—OH | 8.2 | 5.7 | — | >10 |
| 2. Dmt—Tic—NH$_2$ | 7.2 | 4.2 | — | >10 |
| 5. Dmt—Tic—CH$_2$OH | 7.0 | 6.6 | — | >10 |
| 6. c(Dmt—Tic) | 5.43 | 3,800 | — | 20.0 ± 2 |
| 8. Dmt—Tic—Ala—OH | 8.4 | 4.0 | — | >10 |
| 9. Dmt—Tic—Ala—NH$_2$ | 8.0 | 9 | — | 4.74 ± 0.9 |
| Naltrindole | 9.2 | 0.7 | 7.3 | 53 |

Table Legend for Figure VI. MVD = mouse vas deferens assay; GPI gunea-pig illium.

TABLE VII

Internal coordinates of low energy conformers of Tyr-Tic-OH, Dmt-Tic-OH and c(Dmt-Tic).

| Cluster | $^a$Frequency | $^b$Energy | *Ψ$_1$ | χ$_{11}$ | χ$_{12}$ | φ$_2$ | χ$_{21}$ | χ$_{22}$ |
|---|---|---|---|---|---|---|---|---|
| Tyr-Tic-OH | | | | | | | | |
| I | 151 | −158.4 | 142.8 | −98.4 | 63.1 | 123.7 | −180.0 | 75.0 |
| II | 92 | −146.9 | 159.3 | −80.0 | −46.7 | 130.6 | −176.7 | 79.7 |
| III | 101 | −141.3 | 148.4 | −91.7 | 172.5 | 111.5 | −174.5 | 70.5 |
| Dmt-Tic-OH | | | | | | | | |
| I | 210 | −123.1 | 146.7 | −94.6 | 66.8 | 123.0 | 180.0 | 75.0 |
| II | 79 | −113.1 | 147.1 | −94.2 | 64.8 | 121.3 | 72.2 | 75.8 |
| III | 71 | −108.1 | 147.3 | −93.7 | 63.7 | 119.8 | −164.9 | 67.4 |
| IV | 101 | −105.8 | 145.5 | −94.2 | −177.4 | 108.5 | −173.9 | 70.0 |
| c(Dmt-Tic) | | | | | | | | |
| I | 167 | 51.4 | 19.7 | −107.6 | 65.4 | −12.5 | −110.9 | 160.7 |
| II | 225 | 54.7 | 22.3 | −101.2 | −55.1 | −17.5 | −106.6 | 169.3 |
| III | 205 | 55.1 | 17.3 | −106.9 | −178.8 | −17.1 | −107.5 | 171.2 |

Table Legend for FIG. VII.
$^a$Number of times that this conformation occurred during analysis of 3000 structures.
$^b$Potential energy reported in kJ/mol.
*Dihedrals (Ψ, χ, φ) are within ± 0.1 degrees.

References

1. Schiller, P. W. (1984) Prog. Med. Chem. 28, 301–340.
2. Hruby, V. J., and Gehrig, C. A. (1989) Med. Res. Rev. 9, 343–401.
3. Erspamer, V. (1992) Int. J. Dev. Neurosci. 10, 3–30.
4. Chen, Y., Mestek, A., Liu, J., Hurley, J. A., and Yu, L. (1993) Mol. Pharmacol. 44, 8–12.
5. Fukuda, K., Kato, S., Mori, K., Nishi, M., and Takeshima, H. (1993) FEBS Lett. 327, 311–314.
6. Evans, C. J., Keith Jr., D. E., Morrison, H., Magendzo, K., and Edwards, R. H. (1992) Science 258, 1952–1955.
7. Kieffer, B. L., Befort, K., Gaveriaux-Ruff, C., and Hirth, C. G. (1992) Proc. Natl. Acad. Sci. 89, 12048–12052.
8. Yasuda, K., Raynor, K., Kong, H., Breder, C. D., Takeda, J., Reisine, T., and Bell, G. I. (1993) Proc. Natl. Acad. Sci. 90, 6736–6740.
9. Fukuda, K., Kato, S., Mori, K., Nishi, M., Takeshima, H., Iwabe, N., Miyata, T., Houtani, T., and Sugimoto, T. (1994) FEBS. Lett. 343, 42–46.
10. Knapp, R. J., Malatynska, E., Fang, L., Li, X., Babin, E., Nguyen, M., Santoro, G., Varga, E. V., Hruby, V. J., Roeske, W. R., and Yamamura, H. I. (1994) Life Science 54, PL463–469.
11. Abood, M. E., Noel, M. A., Farnsworth, J. S., and Tao, Q. (1994) J. Neurosci. Res. 37, 714–719.
12. Wang, J. B., Imai, Y., Eppler, C. M., Gregor, P., Spivak, C. E., and Uhl, G. R. (1994) Proc. Natl. Acad. Sci. 90, 10230–10234.
13. Chen, Y., Mestek, A., Liu, J., and Yu, L. (1993) Biochem. J. 295, 625–628.
14. Li, S., Zhu, J., Chen, C., Chen, Y.-W., Deriel, J. K., Ashby, B., and Liu-Chen, L.-Y. (1993) Biochem. J. 295, 629–633.
15. Meng, F., Xie, G.-X., Thompson, R. C., Mansour, A., Goldstein, A., Watson, S. J., and Akil, H. (1993) Proc. Natl. Acad. Sci. 90, 9954–9958.
16. Bilsky, E. J., Bernstein, R. N., Pasternak, G. W., Hruby, V. J., Patel, D., Porreca, F., and Lai, J. (1994) Life Science 55, PL37–43.
17. Lai, J., Bilsky, E. J., Rothman, R. B., and Porecca, F. (1994) NeuroReport 5, 1049–1052.
18. Tseng, L. F., Collins, K. A., and Kampine, J. P. (1994) Eur. J. Pharmacol. 258, R1-R3.
19. Collin, E., and Cesselin, F. (1991) Clin. Neuropharmacol. 14, 465–488.

20. Balboni, G., Marastoni, M., Picone, D., Salvadori, S., Tancredi, T., Temussi, P. A., and Tomatis, R. *Biochem. Biophys. Res. Commun.* 1990, 169, 617–622.

21. Lazarus, L. H., Salvadori, S., Tomatis, R., and Wilson, W. E. (1991) *Biochem. Biophys. Res. Commun.* 178, 110–115.

22. Melchiorri, P., Negri, L., Falconieri Erspamer, G., Severini, C., Corsi, R., Soaje, M., Erspamer, V., and Barra, D. (1991) *Eur. J. Pharm.* 195, 201–207.

23. Sagan, S., Amiche, M., Delfour, A., Camus, A., Mor, A., and Nicolas, P. (1989) *Biochem. Biophys. Res. Commun.* 163, 726–732.

24. Sagan, S., Amiche, M., Delfour, A., Mor, A., Camus, A., and Nicolas, P. (1989) *J. Biol. Chem.* 264, 17100–17106.

25. Marastoni, M., Tomatis, R., Lazarus, L. H., and Salvadori, S. (1991) *Farmaco.* 46, 1273–1279.

26. Sagan, S., Charpentier, S., Delfour, A., Amiche, M., and Nicolas, P. (1992) *Biochem. Biophys. Res. Commun.* 187, 1203–1210.

27. Lazarus, L. H., Salvadori, S., Attila, M., Grieco, P., Bundy, D. M., Wilson, W. E., and Tomatis, R. (1993) *Peptides* 14, 21–28.

28. Amiche, M., Sagan, S., Mor, Delfour, A., and Nicolas, P. (1989) *Mol. Pharmacol.* 35, 774–779.

29. Charpentier, S., Sagan, S., Delfour, A., and Nicolas, P. (1991) *Biochem. Biophys. Res. Commun.* 179, 1161–1168.

30. Mosberg, H. I., and Kroona, H. B. (1992) *J. Med. Chem.* 35, 4498–4500.

31. Schiller, P. W., Weltrowska, G., Nguyen, T. M.-D., Lemieux, C., Chung, N. N., Marsden, B. J., and Wilkes, B. C. (1991) *J. Med. Chem.* 34, 3128–3132.

32. Salvadori, S., Bryant, S. D., Bianchi, C., Balboni, G., Attila, M., and Lazarus, L.H. (1993) *J. Med. Chem.* 36, 3748–3756.

33. Lazarus, L. H., Salvadori, S., Balboni, G., Tomatis, R., and Wilson, W. E. (1992) *J. Med. Chem.* 35, 1222–1227.

34. Lazarus, L. H., Salvadori, S., Grieco, P., Wilson, W. E., and Tomatis, R. (1992) *Eur. J. Med. Chem.* 27, 791–797.

35. Sasaki, Y., Ambo, A., and Susuki, K. (1992) *Biochem. Biophys. Res. Commun.* 180, 822–827.

36. Charpentier, S., Sagan, S., Naim, M., Delfour, A., and Nicolas, P. (1994) *Eur. J. Pharmacol.* 266, 175–180.

37. Schiller, P. W., Nguyen, T. M. D., Weltrowska, G., Wilkes, B. C., Marsden, B. J., Lemieux, C., and Chung, N. N. (1992) *Proc. Natl. Acad. Sci.* 89, 11871–11875.

38. Schiller, P. W., Weltrowska, G., Nguyen, T. M. D., Wilkes, B. C., Chung, N. N., and Lemieux, C. (1993) *J. Med. Chem.* 36, 3182–3187.

39. Temussi, P. A., Salvadori, S., Amodeo, P., Bianchi, C., Guerrini, R., Tomatis, R., Lazarus, L. H., Picone, D., and Tancredi, T. (1994) *Biochem. Biophys. Res. Commun.* 198, 933–939.

40. Lazarus, L. H., Wilson, W. E., de Castiglione R., and Guglietta, A. (1989) *J. Biol. Chem.* 264, 3047–3050.

41. Bryant, S. D., Attila, M., Salvadori, S., Guerrini, R., and Lazarus, L. H. (1994) *Peptide Res.* 7: 175–184.

42. Lazarus, L. H., Salvadori, S. Santagada, V., Tomatis R., and Wilson, W. E. (1991) *J. Med. Chem.* 34, 1350–1359.

43. Bryant, S. D., Salvadori, S., Attila, M., and Lazarus, L. H. (1993) *J. Amer. Chem. Soc.* 115, 8503–8504.

44. Dygos, J. H., Yonan, E. E., Scaros, M. G., Goodmonson, O. J., Getman, D. P., Periana, R. A., and Beck, G. R. (1992) *Synthesis* 8, 741–743.

45. Chandrakumar, N. S., Yonan, P. K., Stapelfeld, A., Savage, M., Rorbacher, E., Contreras, P. C., and Hammond, D. (1992) *J. Med. Chem.* 35, 223–233.

46. Pettit, G. R. *Synthetic Peptides*, Vol. 4, New York, Van Nostrand Reinhold (1976).

47. Yamaguchi, R., Hamasaki, T., Sasaki, T., Ohta, T., Utimoto, K., Kozima, S., and Takaya, H. (1993) *J. Org. Chem.* 58, 1136–1143.

48. Cheng, Y. C., and Prusoff, W. H. (1973) *Biochem. Pharmacol.* 22, 3099–3108.

49. Attila, M., Salvadori, S., Balboni, G., Bryant, S. D., and Lazarus, L. H. (1993) *Int. J. Peptide Prot. Res.* 42, 550–559.

50. Kosterlitz, H. W., Lees, G. M., Wallis, D. I., and Watt, A. J. (1968) *Br. J. Pharmacol.* 34, 691P-692P.

51. Schild, H. O. (1947) *Br. J. Pharmacol.* 2, 189–206.

52. Harris, D. P. Burton, R., and Sinclair, J. G. (1988) *J. Pharmacol. Meth.* 20, 103–108.

53. Hylden, J. L. K., and Wilcox, G. L. (1980) *Eur. J. Pharmacol.* 67, 313–316.

54. Sing, U. C., Weiner, P. K., Caldwell, J. W., and Kollman, P. A. AMBER (v. 3.0, rev. A). (1988) Dept. Pharm. Chem., University of California, San Francisco.

55. Darden, T., Johnson, P., and Smith, H. (1991) *J. Mol. Graphics* 9, 18–23, 35.

56. Hammond, D. L., Stapelfeld, A., Drower, E. J., Savage, M. A., Tam, L., and Mazur, R. H. (1994) *J. Pharmacol. Exper. Ther.* 268, 607–615.

57. Schiller, P. W., Weltrowska, G., Nguyen, T. M.-D., Wilkes, B. C., Chung, N. N., and Lemieux, C. (1992) *J. Med. Chem.* 35, 3956–3961.

58. Portoghese, P. S., Sultana, M., Moe, S. T., and Takemori, A. E. (1994) *J. Med. Chem.* 37, 579–585.

59. Portoghese, P. S., Moe, S. T., and Takemori, A. E. (1993) *J. Med. Chem.* 36, 2572–2574.

60. Toth, G., Russell, K. C., Landis, G., Kramer, T. H., Fang, L., Knapp, R., Davis, P., Burks, T. F., Yamamura, H. I., and Hruby, V. J. (1992) *J. Med. Chem.* 35, 2384–2391.

61. Portoghese, P. S. (1989) *Trends Pharmacol. Sci.* 10, 230–235.

62. Castiglione-Morelli, M. A., Lelj, F., Pastore, A., Salvadori, S., Tancredi, T., Tomatis, R., Trivellone, E., and Temussi, P. A. (1987) *J. Med. Chem.* 37, 2067–2073.

63. Tourwe, D., Verschueren, D., Van Binst, G., Davis, P., Porreca, F., and Hruby, V. J. (1992) *Bioorg. Med. Chem. Lett.* 2, 1305–1308.

64. Terenius, L. (1976) *Eur. J. Pharmacol.* 38, 211–213.

65. Kazmierski, W., Wire, S. W., Lui, G. K., Knapp, R. J., Shook, J. E., Burks, T. F., Yamamura, H. I., and Hruby, V. J. (1988) *J. Med. Chem.* 31, 249–253.

66. Deeks, T., Crooks, P. A., and Waigh, R. D. (1983) *J. Med. Chem.* 26, 762–765.

67. Chandrakumar, N. S., Stapelfeld, A., Beardsley, P. M., Lopez, O. T., Drury, B., Anthony, E., Savage, M. A., Williamson, L. N., and Reichman, M. (1992) *J. Med. Chem.* 35, 2928–2938.

68. Pizele, B. S., Hamilton, R. W., Kudla, K. D., Tsymbalov, S., Stapelfeld, A., Savage, M. A., Clare, M., Hammond, D. L., and Hansen, Jr., D. W. (1992) *J. Med. Chem.* 37, 888–896.

69. Hansen, Jr., D. W., Stapelfeld, A., Savage, M. A., Reichman, M., Hammond, D. L., Haaseth, R. C., and Mosberg, H. I. (1992) *J. Med. Chem.* 35, 684–687.

70. Qian, X., Kövér, K. E., Shenderovich, M. D., Lou, B.-S., Misicka, A., Zalewska, T., Horváth, R., Davis, P., Bilsky, E. J., Porreca, F., Yamamura, H. I., and Hruby, V. J. (1994) *J. Med. Chem.* 37, 1746–1757.

71. Smith, G. D., and Griffin, J. F. (1978) *Science* 199, 1214–1216.

72. Horn, A. S., and Rodgers, J. R. (1976) *Nature*, 260, 795–797.

73. Feinberg, A. P., Creese, I., and Snyder, S. H. (1976) *Proc. Natl. Acad. Sci.* 73, 4215–4219.
74. Gorin, F. A., and Marshall, G. R. (1977) *Proc. Natl. Acad. Sci.* 74, 5179–5183.
75. Roques, B. P., Garbay-Jaureguiberry, C., Oberlin, R., Anteunis, M., and Lala, A. K. (1976) *Nature* 276, 778-779-76.
76. Bradbury, A. F., Smyth, D. G., and Snell, C. R. (1976) *Nature* 260, 624–625.
77. Schiller, P. W., and DiMaio, J. (1982) *Nature* 297, 74–76.
78. Mosberg, H. I., Hurst, R., Hruby, V. J., Gee, K., Yamamura, H. I., Galligan, J. J., and Burks, T. (1980) *Proc. Natl. Acad. Sci.* 80, 5871–5876.
79. Temussi, P. A., Picone, D., Tancredi, T., Tomatis, R., Salvadori, S., Marastoni, M., and Balboni, G. (1989) *FEBS Lett.* 247, 283–288.
80. Portoghese, P. S. (1965) *J. Med. Chem.* 8, 609–616.
81. Lazarus, L. H., Wilson, W. E., Gaudino, G., Irons, B., and Guglietta, A. (1985) *Peptides* 6 (Suppl. 3), 295–307.
82. Lazarus, L. H., and Attila, M. (1993) *Prog. Neurobiol.* 41, 473–507.
83. Beckett, A. H. (1956) *J. Pharm. Pharmacol.* 8, 848–8
84. Schwyzer, R. (1986) *Biochemistry* 25, 6335–6342.
85. Pastore, A., Tancredi, T., and Temussi, P. A. (1985) *Peptides Structure and Function*, eds. Deber, C. M., Hruby, V. J., and Kople, K. D., *Proc.* 9$^{th}$ *Amer. Peptide Symp.*, pp. 529–532.
86. Schwyzer, R. (1977) *Ann. N. Y. Acad. Sci.* 297, 3–26.
87. Toll, L., Keys, C., Polgar, W., and Loew, G. (1984) *Neuropeptides* 5:205–208.
88. Pattabiraman, N., Sorensen, K. R., Langridge, R., Bhatnagar, R. S., Renugopalakrishnan, V., and Rapaka, R. S. (1986) *Biochem. Biophys. Res. Commun.* 140, 342–349.
89. Amodeo, P.; Motta, A.; Tancredi, T.; Salvadori, S.; Tomatis, R.; Picone, D.; Saviano, G.; Temussi, P. A. (1992) *Peptide Res.* 5, 48–55.
90. Tancredi, T., Temussi, P. A., Picone, D., Amodeo, P., Tomatis, R., Salvadori, S., Marastoni, M., Santagada, V., and Balboni, G. (1991) *Biopolymers* 31, 751–760.
91. Lazarus, L. H., Wilson, W. E., Guglietta, A., and de Castiglione, R. (1990) *Mol. Pharmacol.* 37, 886–892.
92. Schiller, P. W., Nguyen, T. M.-D., Chung, N. N., and Lemieux, C. (1989) *J. Med. Chem.* 32, 698–703.
93. Tancredi, T., Salvadori, S., Amodeo, P., Picone, D., Lazarus, L. H., Bryant, S. D., Guerrini, R., Mazzola, G., and Temussi, P. A. (1994) *Eur. J. Biochem* 224, 241–247.
94. Surratt, C. K., Johnson, P. S., Moriwaki, A., Seid Leck, B. K., Blaschak, C. J., Wang, J. B., and Uhl, G. R. (1994) *J. Biol. Chem.* 269, 20548–20553.

---

We claim:

1. A Dmt-Tic dipeptide of the formula wherein R is selected from We group consisting of COOH, $CONH_2$, $CONHCH(CH_3)CH_2CH_2CH_3$, CO—NH—NH—(1-adamantanecarbonyl), $CH_2OH$, CO—NH—NH—CO—$CH_3$), cyano, $CO_2CH_3$, $CO_2tBu$, and $CO_2CH_2Ph$.

2. The dipeptide of claim 1 wherein R=—$CH_2OH$.

3. The dipeptide of claim 1 wherein R=—$CONH_2$.

4. The dipeptide of claim 1 wherein R=—COOH.

5. A tripeptide of the formula wherein A-R represents an amino acid residue in peptide linkage to the Tic residue; and wherein R is the terminal COOH group of the amino acid residue, or R replaces the terminal COOH group of the amino acid and is selected from the group consisting of $CONH_2$, $CONHCH(CH_3)CH_2CH_2CH_3$, CO—NH—NH—(1-adamantanecarbonyl), $CH_2OH$, CO—NH—NH—CO—$CH_3$), cyano, $CO_2CH_3$, $CO_2tBu$, and $CO_2CH_2Ph$.

6. The tripeptide of claim 5 wherein said amino acid is any naturally occurring amino acid or its enantiomer.

7. The tripeptide of claim 6 wherein said amino acid is selected from the group consisting of histidine, leucine, isoleucine, valine, cysteine, methionine, serine, threonine, tryptophan, phenylalanine, tyrosine, asparagine, glutamine, lysine, arginine, and proline.

8. The tripeptide of claim 5 wherein said amino acid is selected from the group consisting of aminoisobutyric acid, aminobutyric acid, diaminobutyric acid, γ-carboxyglutamic acid, Tic, 2-aminoindane-2-carboxylic acid (Aic), 2-aminotetralin-2-carboxylic acid (Atc), homophenylalanine (Hfe), 1- and 2-naphthylalanines (Nap), dehydrophenylalanine (ΔPhe), methylphenylalanines, and methylhistidines.

9. The tripeptide of claim 5 wherein said amino acid is alanine and R is COOH.

10. The tripeptide of claim 5 wherein said amino acid is alanine and R is $CONH_2$.

11. A peptide according to claims 1 or 5 capable of binding to the delta (δ) receptor.

12. A peptide according to claims 1 or 5 which is an antagonist of the delta (δ) receptor.

13. A method of treating neuropeptide or neurotransmitter imbalance in a mammal by administering a therapeutically effective amount of a peptide according to claims 1, 2, 3, or 4.

14. A method of treating neuropeptide or neurotransmitter imbalance in a mammal by administering a therapeutically effective amount of a peptide according to claims 5, 6, 7, 8, 9, or 10.

15. A method of treating opiate dependency or alcohol dependency in a mammal comprising administering a therapeutically effective amount of a peptide according to claims 1, 2, 3, or 4.

16. A method of treating opiate dependency or alcohol dependency in a mammal comprising administering a therapeutically effective amount of a peptide according to claims 5, 6, 7, 8, 9, or 10.

17. A pharmaceutical composition comprising a dipeptide according to claims 1, 2, 3, or 4, or a pharmaceutically acceptable salt thereof, in combination with one or more pharmaceutically acceptable carriers.

18. A pharmaceutical composition comprising a tripeptide according to claims 5, 6, 7, 8, 9, or 10, or a pharmaceutically acceptable salt thereof, in combination with one or more pharmaceutically acceptable carriers.

19. A peptide according to claim 1 wherein said peptide is labeled with a radioactive label.

20. The peptide of claim 1 wherein said peptide is coupled to a colorimetric label.

21. A method of labeling δ opiate receptors comprising contacting a labeled peptide of claims 5, 19, or 20 with said δ receptor.

22. The method of claim 21, wherein said method is carried out in vitro.

23. The method of claim 21, wherein said method is carried out in vivo.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 3
        ( B ) TYPE: Amino Acid
        ( C ) STRANDEDNESS: Unknown
        ( D ) TOPOLOGY: Unknown     ( i x ) FEATURE:
        ( D ) OTHER INFORMATION: Tyr-D-Xaa- Phe is the common N Terminal sequence of the amphibian heptapeptides     ( x i ) SEQUENCE DESCRIPTION: SEQ ID NO:1:

Tyr Xaa Phe ( 2 ) INFORMATION FOR SEQ ID NO:2:

( i ) SEQUENCE CHARACTERISTICS:
        ( A ) LENGTH: 4
        ( B ) TYPE: Amino Acid
        ( C ) STRANDEDNESS: Unknown
        ( D ) TOPOLOGY: Unknown     ( i x ) FEATURE:
        ( D ) OTHER INFORMATION: Xaa is tetrahydro-3-isoquinoline carboxylic acid (Tic)

( x i ) SEQUENCE DESCRIPTION: SEQ ID NO:2:

Tyr Xaa Phe Phe ( 2 ) INFORMATION FOR SEQ ID NO:3:

( i ) SEQUENCE CHARACTERISTICS:
        ( A ) LENGTH: 2
        ( B ) TYPE: Amino Acid (C) STRANDEDNESS: Unknown
(D) TOPOLOGY: Unknown (ix) FEATURE:
(D) OTHER INFORMATION: Xaa is tetrahydro-3-
isoquinoline carboxylic acid (Tic)

(xi) SEQUENCE DESCRIPTION: SEQ ID NO:3:

Tyr Xaa (2) INFORMATION FOR SEQ ID NO:4:

(i) SEQUENCE CHARACTERISTICS:
(A) LENGTH: 3
(B) TYPE: Amino Acid
(C) STRANDEDNESS: Unknown
(D) TOPOLOGY: Unknown (ix) FEATURE:
(D) OTHER INFORMATION: Xaa is tetrahydro-3-
isoquinoline carboxylic acid (Tic)

(xi) SEQUENCE DESCRIPTION: SEQ ID NO:4:

Tyr Xaa Ala (2) INFORMATION FOR SEQ ID NO:5:

(i) SEQUENCE CHARACTERISTICS:
(A) LENGTH: 2
(B) TYPE: Amino Acid
(C) STRANDEDNESS: Unknown
(D) TOPOLOGY: Unknown (ix) FEATURE:
(D) OTHER INFORMATION: Xaa- Xaa is a
dipeptide of the formula L/D - Dmt - L/D
- Tic - R'where Dmt is 2', 6'-
dimethyl - L -tyrosine, Tic is
tetrahydro - 3 - isoquinoline carboxylic
acid, and R'is a functional group at
the carboxyl terminus of the peptide (xi) SEQUENCE DESCRIPTION: SEQ ID NO:5:

Xaa Xaa (2) INFORMATION FOR SEQ ID NO:6:

(i) SEQUENCE CHARACTERISTICS:
(A) LENGTH: 3
(B) TYPE: Amino Acid
(C) STRANDEDNESS: Unknown
(D) TOPOLOGY: Unknown (ix) FEATURE:
(D) OTHER INFORMATION: Xaa-Xaa-Xaa is a
tripeptide of the formula L/D - Dmt -
L/D - Tic - R-R'where Dmt is 2', 6'
- dimethyl - L -tyrosine, Tic is
tetrahydro - 3 - isoquinoline carboxylic
acid, R is a natural or unusual amino
acid residue, and R'is a functional
group at the carboxyl terminus of the
peptide (xi) SEQUENCE DESCRIPTION: SEQ ID NO:6:

Xaa Xaa Xaa (2) INFORMATION FOR SEQ ID NO:7:

(i) SEQUENCE CHARACTERISTICS:
(A) LENGTH: 2
(B) TYPE: Amino Acid ( C ) STRANDEDNESS: Unknown
( D ) TOPOLOGY: Unknown ( i x ) FEATURE:
( D ) OTHER INFORMATION: Xaa Xaa is a
cyclic peptide of the formula c(L/D -
Dmt - L/D - Tic) where Dmt is 2', 6'
- dimethyl - L -tyrosine, Tic is
tetrahydro - 3 - isoquinoline
carboxylic acid ( x i ) SEQUENCE DESCRIPTION: SEQ ID NO:7:

Xaa Xaa ( 2 ) INFORMATION FOR SEQ ID NO:8:

( i ) SEQUENCE CHARACTERISTICS:
( A ) LENGTH: 3
( B ) TYPE: Amino Acid
( C ) STRANDEDNESS: Unknown
( D ) TOPOLOGY: Unknown ( i x ) FEATURE:
( D ) OTHER INFORMATION: Xaa-Xaa-Xaa is a
cyclic peptide of the formula c(L/D -
Dmt - L/D - Tic - R) where Dmt is 2', 6'
- dimethyl - L -tyrosine, Tic is
tetrahydro - 3 - isoquinoline carboxylic
acid, and R is a natural or unusual
amino acid ( x i ) SEQUENCE DESCRIPTION: SEQ ID NO:8:

Xaa Xaa Xaa ( 2 ) INFORMATION FOR SEQ ID NO:9:

( i ) SEQUENCE CHARACTERISTICS:
( A ) LENGTH: 3
( B ) TYPE: Amino Acid
( C ) STRANDEDNESS: Unknown
( D ) TOPOLOGY: Unknown ( i x ) FEATURE:
( D ) OTHER INFORMATION: Xaa Xaa-Ala is a
tripeptide of the formula L - Dmt -
L/D - Tic - Ala -NH2 where Dmt is 2',
6'- dimethyl - L - tyrosine, Tic is
tetrahydro - 3 isoquinoline carboxylic
acid ( x i ) SEQUENCE DESCRIPTION: SEQ ID NO:9:

Xaa Xaa Ala ( 2 ) INFORMATION FOR SEQ ID NO:10:

( i ) SEQUENCE CHARACTERISTICS:
( A ) LENGTH: 3
( B ) TYPE: Amino Acid
( C ) STRANDEDNESS: Unknown
( D ) TOPOLOGY: Unknown ( i x ) FEATURE:
( D ) OTHER INFORMATION: Xaa-Xaa-Ala is a
tripeptide of the formula L - Dmt -
L/D - Tic - Ala -OH where Dmt is 2',
6'- dimethyl - L - tyrosine, Tic is
tetrahydro - 3 isoquinoline carboxylic
acid ( x i ) SEQUENCE DESCRIPTION: SEQ ID NO:10:

Xaa Xaa Ala (2) INFORMATION FOR SEQ ID NO:11:

(i) SEQUENCE CHARACTERISTICS:
      (A) LENGTH: 2
      (B) TYPE: Amino Acid
      (C) STRANDEDNESS: Unknown
      (D) TOPOLOGY: Unknown    (ix) FEATURE:
      (D) OTHER INFORMATION: Xaa -Xaa is a cyclic peptide of the formula c(L/D -Xmt -L/D - Yaa) where Xmt can be monomethyl, dimethyl or trimethyl and Yaa can be any natural or unusual amino acid    (xi) SEQUENCE DESCRIPTION: SEQ ID NO:11:

Xaa Xaa (2) INFORMATION FOR SEQ ID NO:12:

(i) SEQUENCE CHARACTERISTICS:
      (A) LENGTH: 3
      (B) TYPE: Amino Acid
      (C) STRANDEDNESS: Unknown
      (D) TOPOLOGY: Unknown

(ix) FEATURE:
      (D) OTHER INFORMATION: Xaa-Xaa-Xaa is a cyclic tripeptide of the formula c(L/D - Xmt -L/D -Yaa -R) where Xmt may be monomethyl, dimethyl or trimethyl and Yaa or R can be any natural or unusual amino acid    (xi) SEQUENCE DESCRIPTION: SEQ ID NO:12:

Xaa Xaa Xaa